(12) United States Patent
Hwang et al.

(10) Patent No.: US 10,366,778 B2
(45) Date of Patent: Jul. 30, 2019

(54) METHOD AND DEVICE FOR PROCESSING CONTENT BASED ON BIO-SIGNALS

(71) Applicant: SAMSUNG ELECTRONICS CO., LTD., Suwon-si (KR)

(72) Inventors: Tae-ho Hwang, Seongnam-si (KR); Mi-young Kim, Suwon-si (KR); Min-su Hwangbo, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 268 days.

(21) Appl. No.: 15/085,266

(22) Filed: Mar. 30, 2016

(65) Prior Publication Data

US 2016/0210407 A1 Jul. 21, 2016

Related U.S. Application Data

(63) Continuation of application No. PCT/KR2014/009210, filed on Sep. 30, 2014.

(Continued)

(51) Int. Cl.
*G06K 9/00* (2006.01)
*G06F 21/32* (2013.01)
(Continued)

(52) U.S. Cl.
CPC .............. *G16B 50/00* (2019.02); *G06F 21/32* (2013.01); *G06K 9/00496* (2013.01);
(Continued)

(58) Field of Classification Search
USPC ......................................................... 726/18
See application file for complete search history.

(56) References Cited

U.S. PATENT DOCUMENTS 4,037,332 A * 7/1977 Petrusinsky ............. G09B 7/00
434/307 R
4,883,067 A * 11/1989 Knispel ................ A61B 5/0482
600/545
(Continued)

FOREIGN PATENT DOCUMENTS

EP 0966919 B1 8/2004
JP 2003-111106 A 4/2003
(Continued)

OTHER PUBLICATIONS

Search Report dated Jan. 13, 2015, issued by the International Searching Authority in counterpart International Patent Application No. PCT/KR2014/009210 (PCT/ISA/210).

(Continued)

*Primary Examiner* — Taghi T Arani
*Assistant Examiner* — Badriodot Champakesanatusptodotgov
(74) *Attorney, Agent, or Firm* — Sughrue Mion, PLLC

(57) ABSTRACT

Provided is a method of processing content based on bio-signals, the method includes: acquiring bio-signals of a user; determining a parameter for altering the characteristics of content or determining a type of content to be output, based on the acquired bio-signals; processing the content or determining the type of content to be output, based on the determined parameter; and outputting the processed content or the determined type of content.

10 Claims, 16 Drawing Sheets

Related U.S. Application Data

(60) Provisional application No. 61/884,296, filed on Sep. 30, 2013.

(51) Int. Cl.
 *G16B 50/00* (2019.01)
 *G06Q 50/22* (2018.01)
 *G16H 50/20* (2018.01)

(52) U.S. Cl.
 CPC ......... *G06K 9/00885* (2013.01); *G06Q 50/22* (2013.01); *G16H 50/20* (2018.01); *G06K 2009/00939* (2013.01)

(56) References Cited

U.S. PATENT DOCUMENTS

| | | | | |
|---|---|---|---|---|
| 5,052,401 A * | 10/1991 | Sherwin | .................... | A61B 3/02 329/358 |
| 5,471,009 A * | 11/1995 | Oba | ..................... | G10H 1/00 704/271 |
| 5,667,470 A * | 9/1997 | Janata | ................... | A61M 21/00 600/28 |
| 6,904,408 B1 * | 6/2005 | McCarthy | ............ | A61B 5/6815 705/2 |
| 7,634,117 B2 * | 12/2009 | Cho | .................... | G07C 9/00158 382/124 |
| 7,873,411 B2 * | 1/2011 | Eda | ..................... | G06F 3/015 600/544 |
| 8,041,801 B2 * | 10/2011 | Nakamura | ............ | G06Q 30/02 709/223 |
| 8,135,957 B2 * | 3/2012 | Dinges | ............... | G06K 9/00885 713/186 |
| 9,189,901 B2 * | 11/2015 | Agrafioti | ................. | G06F 21/40 |
| 9,585,592 B2 * | 3/2017 | Soma | ................... | A61B 5/0478 |
| 9,646,261 B2 * | 5/2017 | Agrafioti | ............... | A61B 5/117 |
| 9,867,548 B2 * | 1/2018 | Le | ............... | A61B 5/04 |
| 2008/0104415 A1 * | 5/2008 | Palti-Wasserman | .... | G06F 21/32 713/186 |
| 2008/0161673 A1 * | 7/2008 | Goodall | ............. | A61B 5/04001 600/409 |
| 2009/0069641 A1 * | 3/2009 | Cho | ....................... | A61B 5/024 600/300 |
| 2009/0192556 A1 * | 7/2009 | Wu | ....................... | A61B 5/0031 607/3 |
| 2010/0179394 A1 * | 7/2010 | Sohn | ....................... | A61B 5/00 600/301 |
| 2010/0196861 A1 * | 8/2010 | Lunner | ................. | H04R 25/505 434/112 |
| 2010/0331649 A1 * | 12/2010 | Chou | ................... | A61B 5/0006 600/364 |
| 2010/0331660 A1 * | 12/2010 | Wada | ....................... | A61B 5/04 600/382 |
| 2011/0150253 A1 * | 6/2011 | Corona-Strauss | ..... | H04R 25/70 381/314 |
| 2012/0007737 A1 * | 1/2012 | Kangas | ................. | H04M 19/04 340/540 |
| 2012/0029379 A1 * | 2/2012 | Sivadas | ................ | A61B 5/0482 600/545 |
| 2013/0009868 A1 * | 1/2013 | Sako | ...................... | G16H 40/63 345/156 |
| 2013/0317382 A1 * | 11/2013 | Le | ............................. | A61B 5/04 600/544 |
| 2013/0317384 A1 * | 11/2013 | Le | ......................... | A61B 5/0482 600/545 |
| 2014/0036055 A1 * | 2/2014 | Soma | ................... | A61B 5/0478 348/77 |
| 2015/0074797 A1 * | 3/2015 | Choi | ....................... | G06F 21/32 726/19 |
| 2015/0199010 A1 * | 7/2015 | Coleman | .............. | A61B 5/0006 345/156 |

FOREIGN PATENT DOCUMENTS

| | | |
|---|---|---|
| JP | 2005-56205 A | 3/2005 |
| JP | 2007-104331 A | 4/2007 |
| KR | 10-2005-0108258 A | 11/2005 |
| KR | 10-0600537 B1 | 7/2006 |
| KR | 10-0747446 B1 | 8/2007 |
| KR | 10-0969233 B1 | 7/2010 |
| KR | 10-2013-0050039 A | 5/2013 |

OTHER PUBLICATIONS

Written Opinion dated Jan. 13, 2015, issued by the International Searching Authority in counterpart International Patent Application No. PCT/KR2014/009210 (PCT/ISA/237).

\* cited by examiner

METHOD AND DEVICE FOR PROCESSING CONTENT BASED ON BIO-SIGNALS

CROSS-REFERENCE TO RELATED APPLICATIONS

This application is a Continuation of International Application No. PCT/KR2014/009210 filed Sep. 30, 2014, which claims priority to U.S. Provisional Application No. 61/884,296 filed Sep. 30, 2013, the disclosure of which is incorporated herein by reference in its entirety.

TECHNICAL FIELD

One or more exemplary embodiments relate to a method and device for processing content based on bio-signals.

BACKGROUND ART

With the advancement of wearable devices, methods and apparatuses for performing an input or authentication using biometric technologies such as fingerprint, iris, and facial recognition are being developed. Input or authentication using biometric technologies not only provides higher security than when using conventional passwords or code patterns but also facilitates user inputs.

In particular, among biometric signals, brainwaves may vary depending on movement of muscles near a user's eyes as well as his or her emotional state or concentration level. Thus, a biometric device may detect a user's current state such as his or her concentration level or emotional state based on measured brainwaves and perform biometric tasks according to the detected current state.

As described above, biometric devices may receive a user input by simply measuring brainwaves without requiring a user's action to perform a specific task, thereby providing more user convenience.

DETAILED DESCRIPTION OF THE INVENTION

Technical Solution

One or more exemplary embodiments include a method and device for processing content based on bio-signals, and more particularly, a method and device for processing content or performing user authentication based on bio-signals including brainwaves.

Advantageous Effects

According to an exemplary embodiment, characteristics of content being reproduced may be altered according to a user's status detected from his or her brainwave signals, thereby allowing the user to identify his or her status and change the status in a positive direction.

According to an exemplary embodiment, a user input is facilitated by not having to input via physical contact, and thus, the convenience of user manipulation may be improved.

According to an exemplary embodiment, by using a user's brainwave signals, user authentication is performed without having to input via physical contact. Thus, the user authentication may be performed in a highly secure and convenient way.

BEST MODE

Figure 1:
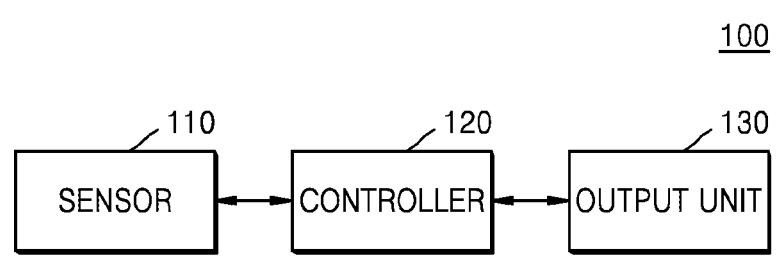
FIG. 1 illustrates an internal configuration of a device for processing content or performing authentication based on bio-signals, according to an exemplary embodiment.

According to one or more exemplary embodiments, a method of processing content based on bio-signals includes: acquiring bio-signals of a user; determining a parameter for altering the characteristics of content or determining a type of content to be output, based on the acquired bio-signals; processing the content or determining the type of content to be output, based on the determined parameter; and outputting the processed content or the determined type of content.

The determining of the parameter may include: determining at least one selected from the group consisting of a user's emotional state, sleep state, stress, workload, and concentration level, based on the acquired bio-signals; and determining a parameter corresponding to the determined user's state.

The bio-signals may include brainwave signals of the user, and the parameter may be determined based on a user's state corresponding to properties of the brainwave signals in a time or frequency domain.

The parameter may include at least one selected from the group consisting of a volume, pitch, playback speed, richness of sound, depth, reverberation, thickness, vibration, sensory effect, surround effect, spatial sense, harmony, chord and accompaniment of the content, a region on a display where the content is displayed, colors, brightness, contrast, transparency, focus, power supply, power consumption of the display, and a type of the content.

The acquiring of the bio-signals of the user may include: outputting at least one object for providing a stimulus to the user and acquiring the bio-signals of the user, which are generated while or after outputting the at least one object. The method may further include detecting at least one object corresponding to a response detected from the bio-signals of the user and performing a task corresponding to the detected at least one object.

The method may further include: determining the user's concentration level based on the acquired bio-signals; obtaining, if the determined user's concentration level is less than a reference point, information about content being reproduced; and providing the obtained information to the user.

The acquiring of the information about the content may include acquiring at least one of main details and summary information of the content at a time point when the user's concentration level decreases to less than the reference point, or recording and storing broadcast content being reproduced.

The providing of the obtained information to the user may include providing the obtained information about the content if the user's concentration level is greater than or equal to the reference point, or according to a user's input.

The information about the content may be acquired based on at least one selected from the group consisting of big data, per-minute audience ratings, and basic information related to the content that are acquired from an external server.

According to one or more exemplary embodiments, a method of performing user authentication based on bio-signals includes: acquiring a bio-signal of a user; detecting a signal pattern to be compared for the user authentication from the acquired bio-signal; performing the user authentication by comparing the detected signal pattern against a signal pattern previously modeled for the user authentication; and updating, if the user authentication is successful, the modeled signal pattern by using the detected signal pattern.

The user authentication may be repeatedly performed while a task requiring the user authentication is being performed.

According to one or more exemplary embodiments, a device for processing content based on bio-signals includes: a sensor configured to acquire bio-signals of a user; a controller configured to determine a parameter for altering the characteristics of content or a type of content to be output based on the acquired bio-signals and process the content or determine the type of content to be output based on the determined parameter; and an output unit configured to output the processed content or the determined type of content.

The sensor may acquire the bio-signals of the user generated while or after outputting at least one object for providing a stimulus to the user, and the controller may detect at least one object corresponding to a response detected from the bio-signals of the user and performs a task corresponding to the detected at least one object.

The controller may determine the user's concentration level based on the acquired bio-signals and obtain, if the determined user's concentration level is less than a reference point, information about content being reproduced, and the output unit may provide the obtained information to the user.

According to one or more exemplary embodiments, a device for performing user authentication based on bio-signals includes: a sensor configured to acquire a bio-signal of a user; a controller configured to detect a signal pattern to be compared for the user authentication from the acquired bio-signal, perform the user authentication by comparing the detected signal pattern against a signal pattern previously modeled for the user authentication, and update, if the user authentication is successful, the modeled signal pattern by using the detected signal pattern; and an output unit configured to output a user authentication result.

MODE OF THE INVENTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. In the following description and accompanying drawings, known functions will not be described in detail so as not to unnecessarily obscure the essence of the present inventive concept.

The terms and words used in the present specification and claims should not be interpreted as being limited to typical meanings or dictionary definitions, but should be interpreted as having meanings and concepts relevant to the technical idea of the present inventive concept based on the rule according to which an inventor can appropriately define the concept of the term to describe most appropriately the best method he or she knows for carrying out the inventive concept. Therefore, the configurations described in the embodiments and drawings of the present inventive concept are merely most preferable embodiments but do not represent all of the technical spirit of the present inventive concept. Thus, the present inventive concept should be construed as including all the changes, equivalents, and substitutions included in the spirit and scope of the present inventive concept at the time of filing this application.

In the accompanying drawings, some components are exaggerated or omitted or schematically illustrated. Further, the size of each element does not entirely reflect an actual size thereof. Exemplary embodiments are not limited by a relative size or spacing drawn in each figure.

Throughout the specification, when a part "includes" or "comprises" an element, the part may further other elements unless specified otherwise. The term "unit" used in the present specification refers to a software component, or a hardware component such as a field-programmable gate array (FPGA) or an application-specific integrated circuit (ASIC), and performs a certain function. However, the "unit" is not limited to software or hardware. The "unit" may be configured in an addressable storage medium and may be configured to operate one or more processors. Hence, the "unit" includes elements such as software elements, object-oriented software elements, class elements, and task elements, and processes, functions, attributes, procedures, subroutines, segments of program codes, drivers, firmware, micro-codes, circuits, data, databases, data structures, tables, arrays, and variables. The functions provided in the elements and the units may be combined into a fewer number of elements and units or may be divided into a larger number of elements and units. Expressions such as "at least one of," when preceding a list of elements, modify the entire list of elements and do not modify the individual elements of the list.

Exemplary embodiments will be described below in detail with reference to the accompanying drawings so that those of ordinary skill in the art may easily implement the inventive concept. The inventive concept may, however, be embodied in many different forms and should not be construed as being limited to the exemplary embodiments set forth herein. In addition, portions irrelevant to the description of the exemplary embodiments will be omitted in the drawings for a clear description of the exemplary embodiments, and like reference numerals will denote like elements throughout the specification.

Accordingly, the exemplary embodiments are merely described below, by referring to the figures, to explain aspects of the present description.

FIG. 1 illustrates an internal configuration of a device 100 for processing content or performing authentication based on bio-signals, according to an exemplary embodiment.

The device 100 measures bio-signals of a user and detects the user's status based on the measured bio-signals. The device 100 may also process content according to the user's status, or determine a reproduction parameter for substituting another type of content with the content to process content by using the determined reproduction parameter.

For example, the device 100 may measure a brainwave signal of a user, determine the user's status such as the user's psychological and mental states and sleep state from the brainwave signal, and process content or substitute another type of content with the content according to the user's status. The device 100 may help improve the user's psychological and mental states by processing content according to the user's status for output. Furthermore, the device 100 may determine at least one content type selected from the group consisting of audio, video, and vibration content according to the user's status and control the determined the at least one content type to be output.

Brainwaves are bio-signals showing the states of activities in the human brain. When a brain nerve cell is activated, an electrical potential difference occurs due to ions such as sodium (Na) and potassium (K) ions that pass through a nerve cell membrane. The brainwaves are a weak flow of electricity caused by the electrical potential difference. Since brain tissue is surrounded by a conductive medium, electric current generated in a neuron may be transmitted to a head surface, and thus, brainwaves may be measured via an electrode attached to a scalp. The device 100 according to the present embodiment may detect a user's status by measuring brainwaves that may vary according to a change in an individual's consciousness and behavior, and process content according to the user's status to be output.

Although the device 100 may measure various types of bio-signals, it is hereinafter described that the device 100 performs a task based on a brainwave signal.

Furthermore, the device 100 may measure bio-signals of a user and perform authentication by using the measured bio-signals. In detail, the device 100 may perform user authentication by detecting a signal pattern for user authentication from the bio-signals and comparing the detected signal pattern with a premodeled signal pattern.

For example, the device 100 may be various types of devices such as mobile phones, tablet PCs, personal digital assistants (PDAs), MP3 players, kiosks, electronic photo frames, navigation devices, digital TVs, and wearable devices such as wristwatches, smart glasses, virtual reality goggles, or head-mounted displays.

Referring to FIG. 1, the device 100 according to the present embodiment includes a sensor 110, a controller 120, and an output unit 130. In the accompanying drawings and exemplary embodiments set forth below, individual components of the device 100 may be separated or integrated in a physical or logical form.

The sensor 110 may acquire bio-signals from a user. The bio-signals may include brainwaves, pulses, an electrocardiogram, etc. If the bio-signals are brainwaves, the sensor 110 may acquire at least one selected from electroencephalogram (EEG), electrooculogram (EOG), electrocardiogram (ECG), electromyogram (EMG), and electrokardiogramm (EKG) signals. The sensor 110 may obtain the bio-signals by contacting the user' body and may come in different forms such as a headset, earphones, and a bracelet.

The controller 120 may perform a task using bio-signals acquired by the sensor 110. In detail, the controller 120 may determine at least one user's state selected from the group consisting of a user's emotional state, a sleep state, and a concentration level and a parameter corresponding to the determined user's state. The parameter may include a reproduction parameter for processing content or determining the type of content or an output parameter for processing a sound signal. The controller 120 may process content or determine the type of content by using the reproduction parameter. If an external sound signal is amplified and output like through a hearing aid, the controller 120 may process the sound signal based on the determined output parameter.

The controller 120 may process content currently being reproduced or a sound signal currently being output according to bio-signals, thereby outputting the content or sound signal processed in real-time according to a change in the user's status. As the content or sound signal processed in real-time are output, the user's status may be changed favorably. Content that may be processed by the controller 120 may include audio or video data. A sound signal may include audio and video signals collected from an external environment. The output unit 130 may output the content such as audio or video data or a sound signal processed by the controller 120 via a display or speaker.

A method of processing content based on bio-signals, according to an exemplary embodiment, will now be described in more detail with reference to FIGS. 2 through 12.

Figure 2:
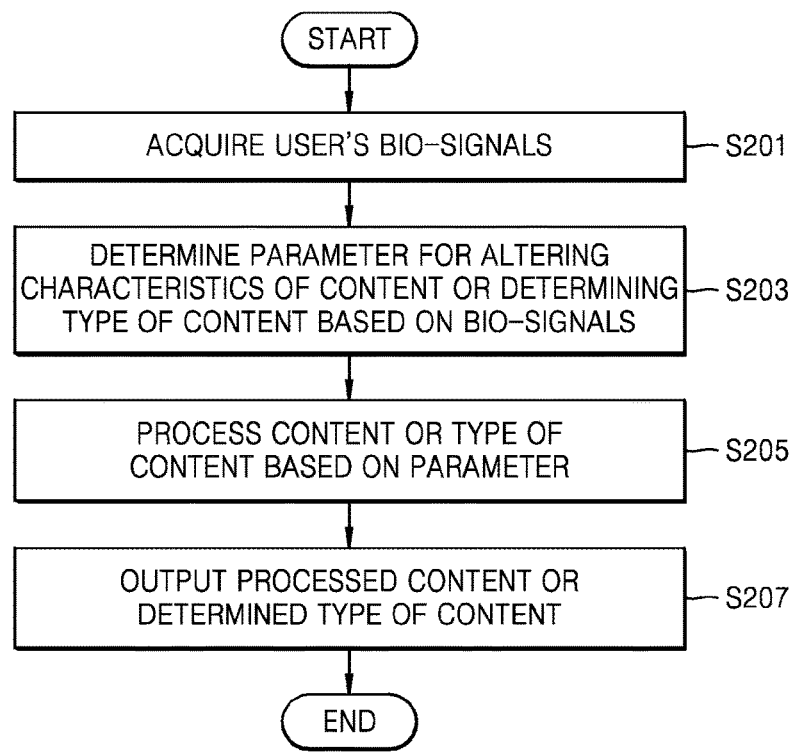
FIG. 2 is a flowchart of a method of processing content based on bio-signals, according to an exemplary embodiment.

FIG. 2 is a flowchart of a method of processing content based on bio-signals, according to an exemplary embodiment.

Referring to FIGS. 1 and 2, the device 100 may acquire bio-signals of a user via the sensor 110 (S201). The bio-signals may be signals that may be used to detect a user's status such as brainwaves, the amount of oxygen in cerebral blood flow, and pulses.

The device 100 may determine a parameter for altering the characteristics of content or a sound signal based on the bio-signals obtained in operation S201 (S203). In detail, the device 100 may determine a user's status based on the bio-signals and a parameter corresponding to the user's status. Furthermore, the device 100 may determine a reproduction parameter for determining the type of content to be output, based on the bio-signals.

The device 100 may process the content or the sound signal by using the parameter determined in operation S203

(S205). For example, the device 100 may alter sound quality, volume, playback speed, richness of sound or color, depth, reverberation, thickness, vibration, sensory effect, surround effect, an equalizer having all these features, spatial sense, saturation, brightness, contrast, transparency, etc. of the content according to the reproduction parameter. Furthermore, the device 100 may determine the type of content to be output by using the reproduction parameter. Like the reproduction parameter, an output parameter for processing a sound signal may include information needed to process the sound signal, such as a quality, volume, pitch, etc. of the sound signal.

According to an exemplary embodiment, like the content, the sound signal that may be collected from the outside, amplified, and output may be processed based on bio-signals of the user. The output parameter that is applied to the sound signal may include the same information as the reproduction parameter. Thus, according to an exemplary embodiment, the method of processing the content is applied in the same way to processing of the sound signal. Processing of the content is considered to include processing of the sound signal, and thus, only processing of the content is described for convenience of description.

The device 100 may output the content that is processed or of which a type is determined in operation S205 via an output device such as a speaker or display (S207).

Figure 3:
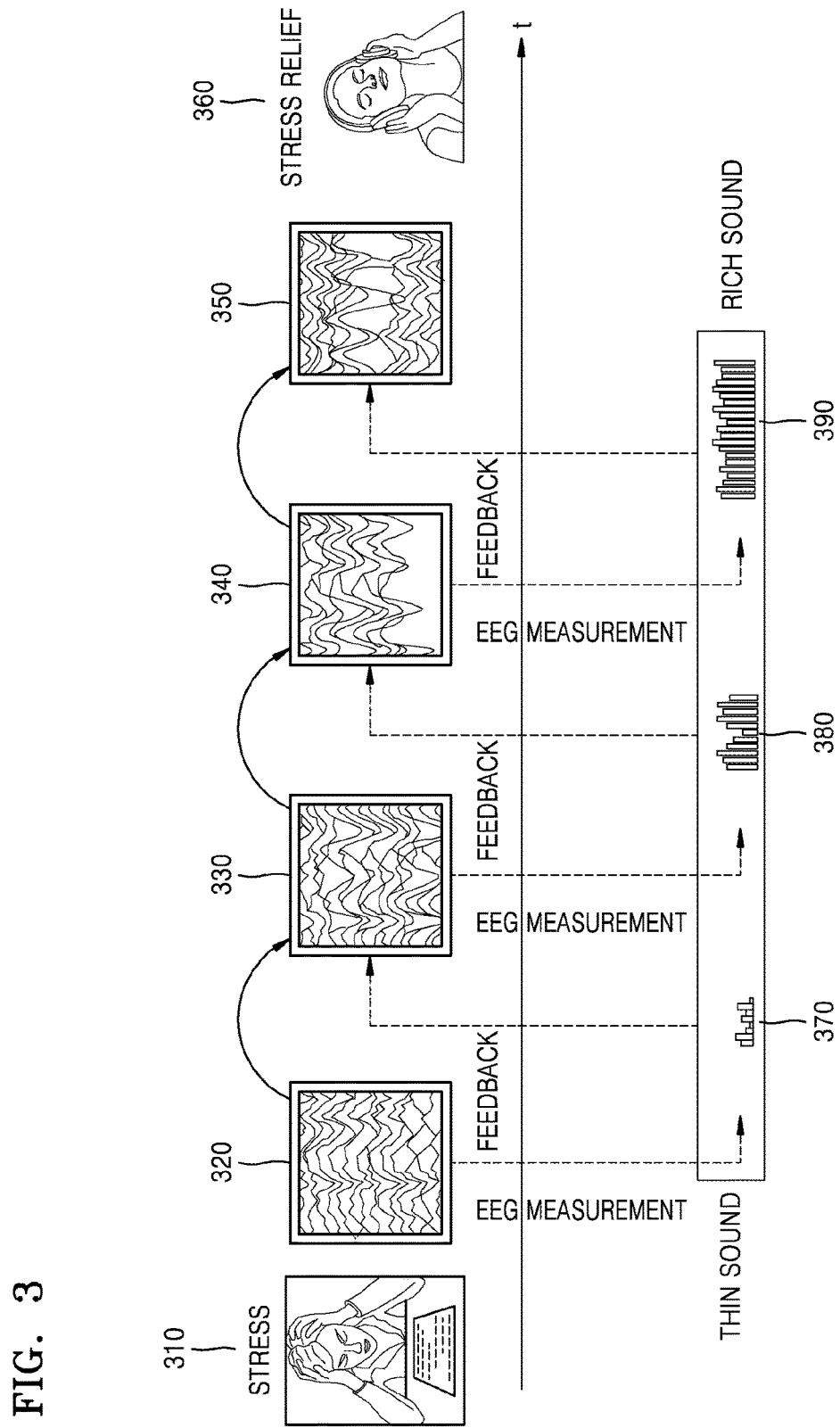
FIG. 3 illustrates an example where content is processed based on bio-signals, according to an exemplary embodiment.

FIG. 3 illustrates an example where content is processed based on bio-signals according to an exemplary embodiment.

Referring to FIGS. 1 and 3, the device 100 may acquire a brainwave signal that is a bio-signal obtained when a user is currently in a stressful state and detect a user's current status based on the brainwave signal. The user's current status that may be detected by the device 100 may include stress, workload, concentration level, and emotional state.

A concentration level refers to the user's level of immersion that may be determined via his or her brainwave signals, the type of immersion, and an object that causes immersion. If the device 100 is an auditory device, the device 100 may detect a direction in which a user concentrates more, among predetermined directions relative to a user's head from which audio or speech signals are obtained, based on bio-signals of the user. In detail, the device 100 may detect asymmetrical brainwave characteristics in which the user's brainwave-signal activates one of the left and right hemispheres of the brain more than the other. The device 100 may detect information about the user's immersion or concentration level and information about a direction in which the user concentrates, based on characteristics of brainwave signals measured at different positions. The device 100 may detect information about a direction for which the user's immersion or concentration level is greater than or equal to a reference value or having the highest priority according to the immersion level as information about a direction in which the user concentrates. The device 100 may receive an external audio or speech signal from one or more spatial directions relative to the user's head, which may be represented as up, down, forward, backward, left, and right directions and combinations thereof.

The device 100 may strengthen an audio or speech signal received from a specific direction in which the user concentrates more than the other directions for output and weaken an audio or speech signal received from the other directions by considering the same as noise. The device 100 may dampen the audio or speech signal considered as noise by using noise cancellation while outputting the strengthened audio or speech signal from the specific direction.

Furthermore, the device 100 may determine an output parameter for processing sound signals including audio and speech signals, based on bio-signals of the user. The device 100 may also process and output strengthened audio and speech signals from a specific direction by using the determined output parameter.

A workload is a measure of how much of the brain is being used that may be determined via a user's brainwave signal. A user's emotional state may include emotional states such as excitation, favorable and unfavorable feelings, and stability. The device 100 may process content in such a manner as to maintain or improve positive psychological and mental health based on a detected user's state. For example, the device 100 may process content so as to improve the user's psychological and mental health in a direction that is generally assessed as positive or the user deems to be positive.

In general, since a brainwave signal can be regulated by an autonomic nervous system, an individual is not able to control the brainwave signal. However, according to the principle of neurofeedback, a brainwave signal may be changed according to an individual's will. Neurofeedback is a technique for controlling the level of activation of desired brainwaves by changing an amplitude of the brainwaves while maintaining a frequency thereof. The neurofeedback technique may measure a user's brainwaves, and, if the user learns to recognize generation of specific brainwaves, strengthen the specific brainwaves automatically recognized. For example, when a sound emanates from a speaker each time alpha waves emerge from measured user's brainwaves, the alpha waves may be increasingly strengthened automatically whenever the sound is output via the speaker. In other words, if a user learns to recognize the measurement of alpha waves each time the alpha waves are measured, the alpha waves may become increasingly stronger whenever a user is informed of measurement of alpha waves. The principle of neurofeedback is similar to a conditional reflex in which if food is given to a dog when a bell is rung, the dog eventually produces saliva when it hears the bell ring. The device 100 may change a user's mental state in a positive direction previously defined by outputting content that is processed so that the user's current state may be identified by using a neurofeedback technique.

The device 100 may measure EEG signals as one type of brainwave signals. An EEG device may be integrated with a listening device such as a headset, an earphone, a hearing aid, or an osteophony headphone, or may be equipped with a sensor that is attached to a head or another body part and connected to the listening device and the device 100 by wire or wirelessly. If the EEG device is integrated with the listening device, it may be inserted into an ear. Brainwaves may be measured via ECG, EOG, EMG, and EKG as well as EEG.

The device 100 may be realized in the form of earphones to output content such as music or audio or a voice for phone conversation, or function like a hearing aid to improve the user's listening capability by amplifying audio and speech signals detected from the outside. The device 100 may process content and audio and speech signals detected from the outside or for phone conversation by using a reproduction parameter determined based on bio-signals of a user.

Transition between above-described functions of the device 100 may be performed by manual manipulation according to a user's will, or automatically based on the user's activity or bio-signals detected by the device 100.

That is, the device 100 may automatically switch the functions based on an input signal or bio-signal that indicates the user's will.

Instead of outputting a specific sound or image for changing brainwaves, the device 100 may process content currently being reproduced or selected by a user according to a user's status to change a user's emotional state and brainwave state. The content that may be processed by the device 100 may include various types of data such as audio, video, a user interface (UI) screen, a graphics screen, and virtual reality.

The device 100 may obtain values of amplitude in a time domain, power in a frequency domain, or power for each time from measured brainwave signals and determine a user's status based on the values.

The device may then determine a reproduction parameter corresponding to the user's status and process content according to the determined reproduction parameter to be output.

The reproduction parameter may include similar properties to sound field effect generated by an equalizer, such as a volume, pitch, playback speed, richness of sound, depth, reverberation, thickness, vibration, sensory effect, surround effect, spatial sense, harmony, chord, and accompaniment of the content. The reproduction parameter may further include notes, chord accompaniment, and musical instrument sounds that may be overlaid over the content.

To maintain or improve a user's psychological and mental states, if the user is in a negative state, sound or images of content currently being reproduced may be processed to have characteristics that are not generally liked. For example, the negative state may include high stress or workload, low concentration level, or unfavorable emotional state. According to the principle of neurofeedback, a user is able to recognize that he or she is currently in a negative state from the content processed by the device 100. The user who learns to recognize the current negative state may change his or her mental state into a positive state by consciously or unconsciously regulating brainwaves. Although the user may initially make a conscious effort to change his or her brainwaves, he or she may unconsciously alter ultrasound waves in a positive way by listening or watching negative content via repeated training.

A user's status may be subdivided into at least two stages and determined as a combination of one or more states. The device 100 may process content according to the user's status to be output.

Referring to FIG. 3, the device 100 may measure a user's brainwaves to determine that the user is in a high stress state 310. The device 100 may process music currently being reproduced as thin sounds 370 so that the user may recognize that he or she is in the high stress state 310 (320). The device 100 allows the user to identify his or her state while listening to the music by altering the characteristics of the music according to the user's state.

The device 100 may measure brainwave signals at short time intervals of 1 to 5 seconds, and process content according to the brainwave signals, based on adjustment sensitivity set by the user or determined according to a predetermined algorithm. That is, like in 320, the device 100 may determine a user's status via measurement of brainwaves and process the music currently being reproduced to output sounds 380 and 390 (330, 340, and 350).

When the user learns to recognize the content processed by the device 100, he or she may unconsciously change his or her state gradually to a relaxed state 360. As the user's status changes to the relaxed state 360, the device 100 may process the music currently being reproduced to output the rich sounds 390.

The device 100 may process content by overlaying sounds such as chord accompaniment, musical instrument sounds, and specific notes over the content instead of changing the content itself.

A method of providing content information according to a user's bio-signals will now be described in detail with reference to FIGS. 4 and 5.

Figure 4:
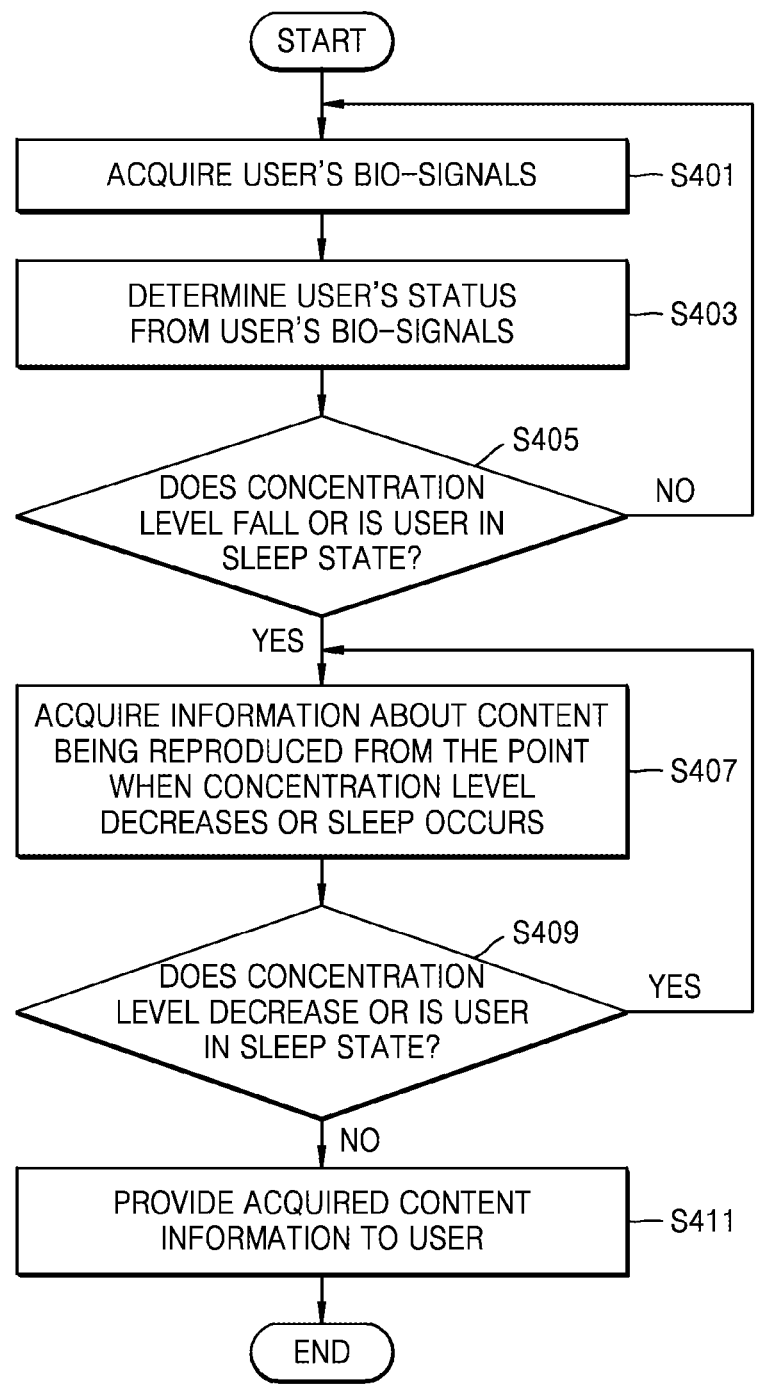
FIG. 4 is a flowchart of a method of providing content information, according to a user's bio-signals according to an exemplary embodiment.

FIG. 4 is a flowchart of a method of providing content information according to bio-signals of a user, according to an exemplary embodiment.

Referring to FIGS. 1 and 4, the device 100 may acquire bio-signals of a user (S401). The bio-signals may be signals used to detect a user's status, such as brainwaves and pulses.

The device 100 may determine a user's status from the bio-signals acquired in operation S401 (S403) to identify whether a user's concentration level falls to a level less than a reference point or the user is in a sleep state (S405). The reference point may be set by the user or automatically according to a default setting of a program. If the user's concentration level continues to be less than the reference point for a predetermined time, the device 100 may determine that the user is in a drowsy state or the user's concentration level is low and thus start to obtain information about content.

Otherwise, if the user's concentration level is greater than or equal to the reference point in operation S405, the device 100 may repeatedly measure bio-signals of the user in operation S401. In this way, the device 100 may periodically or repeatedly measure bio-signals of the user and determine the user's status.

On the other hand, if the user's concentration level falls to a level less than the reference point or the user is in a sleep state in operation S405, the device 100 may obtain information about content currently being reproduced from a time point when the user's concentration level decreases to less than the reference point or the user's status changes to a sleep state (hereinafter, referred to as a 'particular time point') (S407).

In detail, the device 100 may start recording of the content in various ways from the particular time point in order to obtain information about the content.

For example, the device 100 may record details of the content reproduced after the particular time point. If the content is broadcast content, the device 100 may record the details of the content by recording and storing the broadcast content reproduced after the particular time point. If the user's concentration level decreases to less than the reference point or the user's status changes to a sleep state while content stored in a recording medium is being reproduced, the device 100 may record details of the content by recording a position of the content corresponding to the particular time point.

As another example, the device 100 may record details of content by generating a summary of content acquired from big data related to the content, including main highlight scenes and basic information of the content. The big data may include information about the content currently being reproduced among pieces of information on the Internet, such as a social networking service (SNS) or web pages, blogs, and Internet news articles. The device 100 may select scenes with high per-minute audience ratings or being tagged many times among the big data as main highlight scenes. The main highlight scenes may include scenes in content reproduced after a time point when a user's concentration level decreases to less than a reference point or a user's status changes to a sleep state. Big data, per-minute audience ratings, and basic information related to the content may be acquired from an external server.

If the device 100 determines that the user's concentration level increases or a user is out of a sleep state (S409) or according to a user's input, the device 100 may stop recording of content and provide the user with the information about the content acquired in operation S407 (S411). In detail, the device 100 may output recorded details of the content, i.e., recorded and stored broadcast content, or output the content from a recorded position thereof by loading the content stored in a storage medium. The device 100 may also output a summary of content including main highlight scenes or a brief description of the content.

In addition, if the device 100 determines that a user's concentration level decreases to less than a reference point or a user's status changes to a sleep state, the device 100 may control a display to enter a power save mode. If the display goes into a power save mode, the display is turned off, or a screen thereof may darken. In this case, the device 100 may also turn off the power of the display or change characteristics of sound or images. For example, the device 100 may make an image appear darker or turn down a volume of a sound.

Figure 5:
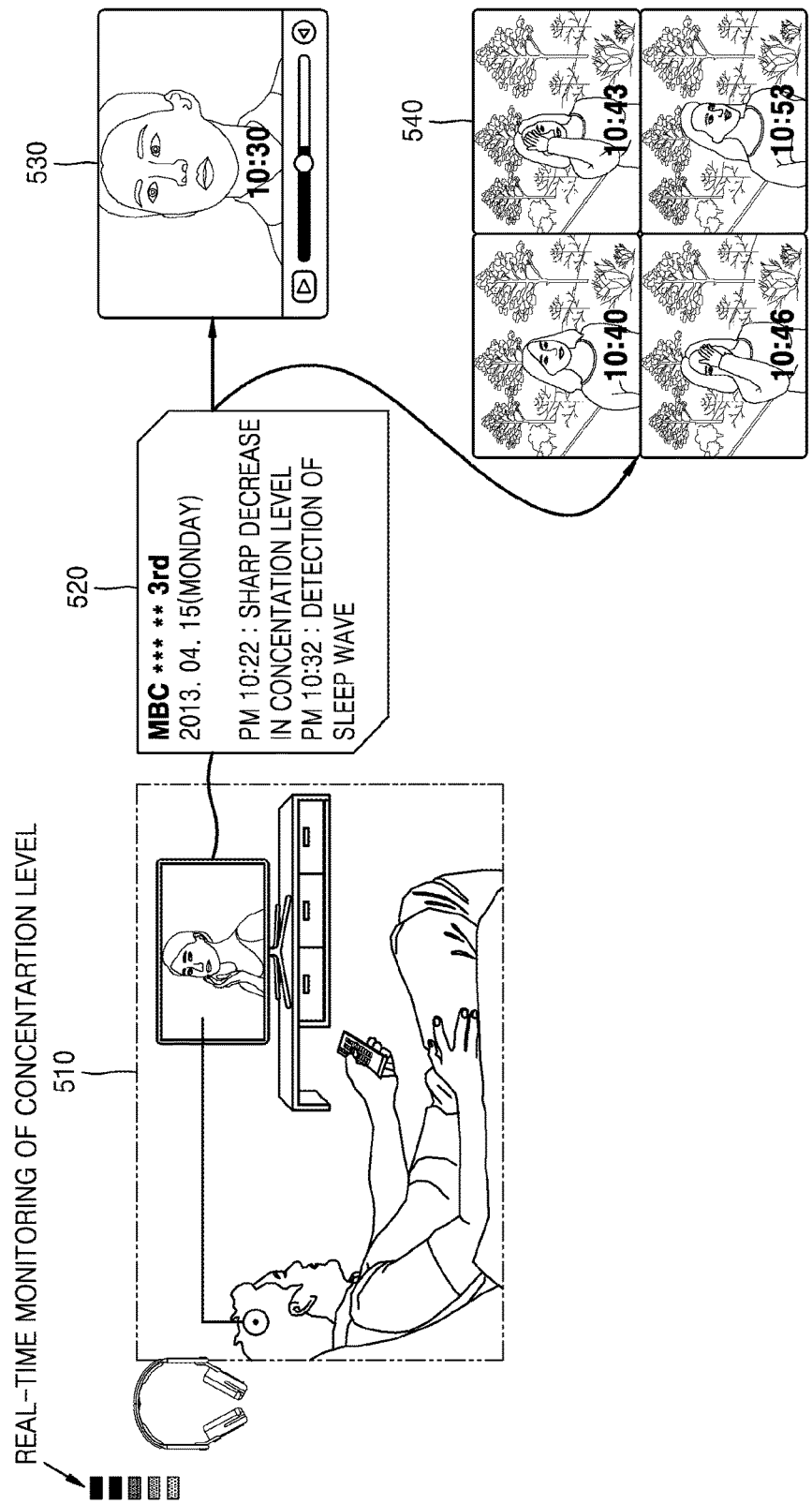
FIG. 5 illustrates an example where content information is provided according to a user's bio-signals, according to an exemplary embodiment.

FIG. 5 illustrates an example where content information is provided according to bio-signals of a user according to an exemplary embodiment.

Referring to FIGS. 1 and 5, the device 100 may monitor a user's status in real-time in order to obtain bio-signals of the user (510). When content is being reproduced, as shown in 510, the device 100 may monitor the user's status by periodically acquiring the bio-signals of the user.

If the user's concentration level determined based on the bio-signals of the user decreases, or the user is in a sleep state (520), the device 100 may start recording of the content (530 and 540). As shown in 520, the device 100 may perform recording of the content from a time point when the user's concentration level decreases or the user goes into a sleep state.

As shown in 530, the device 100 may record and store broadcast content reproduced after the user's concentration level decreases or the user goes into a sleep state. If the content is stored on a recording medium, the device 100 may also record a position of the content reproduced at a time point when the user's concentration level decreases or the user goes into a sleep state.

Furthermore, the device 100 may record main scenes of content reproduced after the time point when the user's concentration level decreases or the user goes into a sleep state (540). The main scenes may be recorded as a short video clip or an image including an image frame.

A method of displaying content by changing a display region of the content according to bio-signals of a user will now be described in detail with reference to FIGS. 6 and 7.

Figure 6:
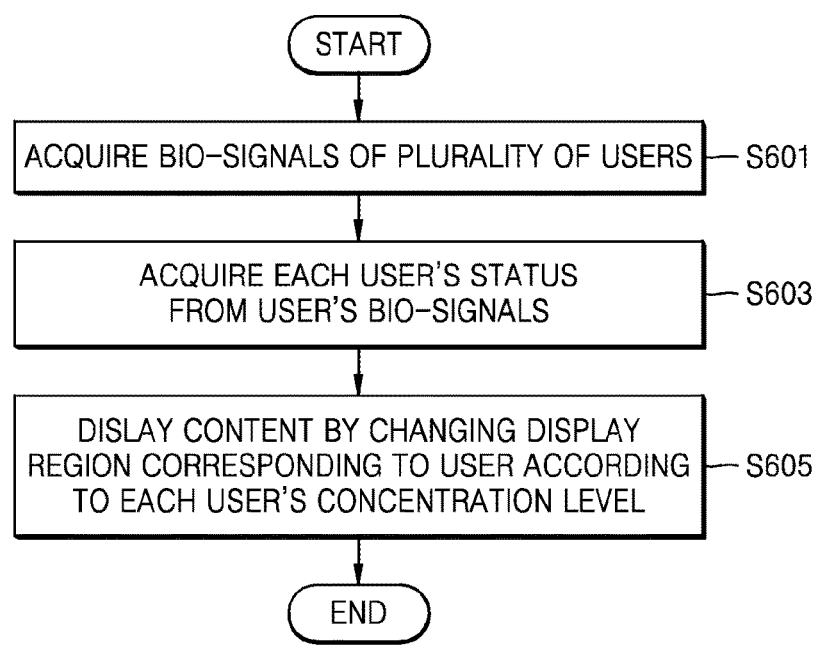
FIG. 6 is a flowchart of a method of displaying content according to a user's bio-signals, according to an exemplary embodiment.

FIG. 6 is a flowchart of a method of displaying content according to bio-signals of a user, in accordance with an exemplary embodiment.

Referring to FIGS. 1 and 6, the device 100 may acquire bio-signals of a plurality of users (S601). The bio-signals may be signals used to detect a user's status, such as brainwaves and pulses. For example, the brainwaves may be obtained by extracting brainwave signals such as EEG, EOG, and ECG signals. The plurality of users from which the bio-signals may be obtained may be watching content being reproduced. The content that may be displayed as shown in FIGS. 6 and 7 may include video or audio data, a UI screen, a graphics screen, etc.

The device 100 may acquire each user's status from the bio-signals acquired in operation S601 (S603). In detail, the device 100 may acquire each user's concentration level from the bio-signals. Each user's concentration level may be represented by a numerical value that is compared with that of another user for analysis.

The device 100 may display content by changing a size of a display region corresponding to each user according to each user's concentration level (S605). In detail, the device 100 may determine a priority based on the user's concentration level, and then a size and position of a display region for each user according to the priority. A relative size of a display region compared to another may be determined according to the priority. The device 100 may then display content corresponding to each user in a display region of which the size and position are determined according to each user's concentration level. Thus, content of a user having the highest priority may be displayed on the largest display region on a display.

Figure 7:
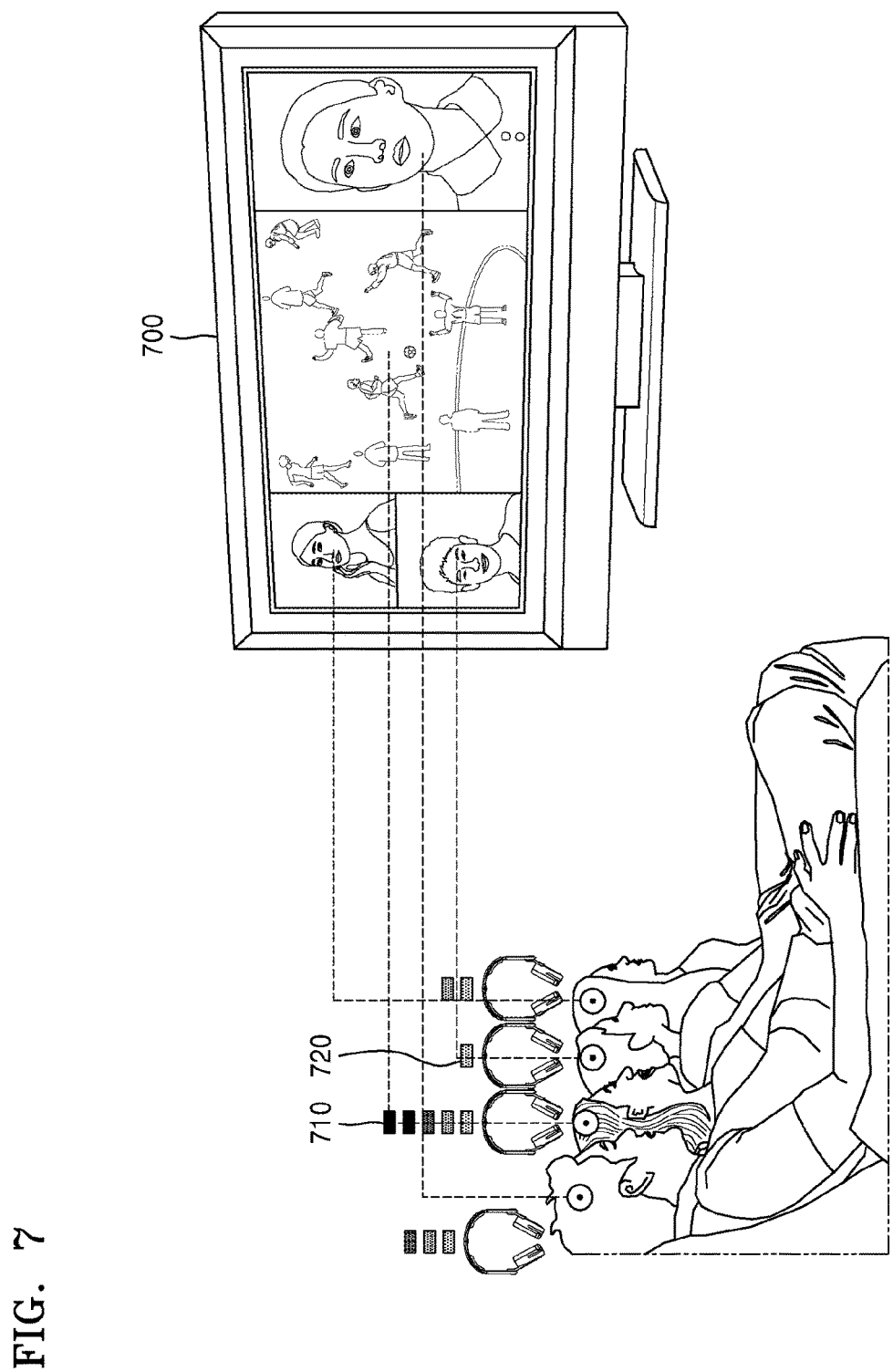
FIG. 7 illustrates an example where content is displayed according to a user's bio-signals, in accordance with an exemplary embodiment.

FIG. 7 illustrates an example where content is displayed according to bio-signals of a user, in accordance with an exemplary embodiment.

Referring to FIGS. 1 and 7, the device 100 may control a display 700 to display content corresponding to a user 710 showing the highest concentration level on a largest region thereon. Furthermore, the device 100 may control the display 700 to display content corresponding to a user 720 showing the lowest concentration level in a smallest region thereon.

A size of a display region determined according to each user's concentration level may be changed in real-time as the bio-signals of the user are obtained. Furthermore, a user's concentration level may be compared against another user's concentration level by displaying content having a size that is proportional to the other user's concentration level together on the display.

When four members of a family are watching a large-screen TV at the same time as shown in FIG. 7, four different types of content may be displayed on display regions having different sizes according to each member's concentration level. Furthermore, a size of a display region may be changed in real-time according to a change in each member's concentration level.

As another example, if four family members are playing games together via a large-screen display, different game screens may be displayed in different sizes according to each member's concentration level. Each family member may hear sounds of a game screen or content that he or she is viewing via separate audio output devices such as headsets or earphones.

Figure 8:
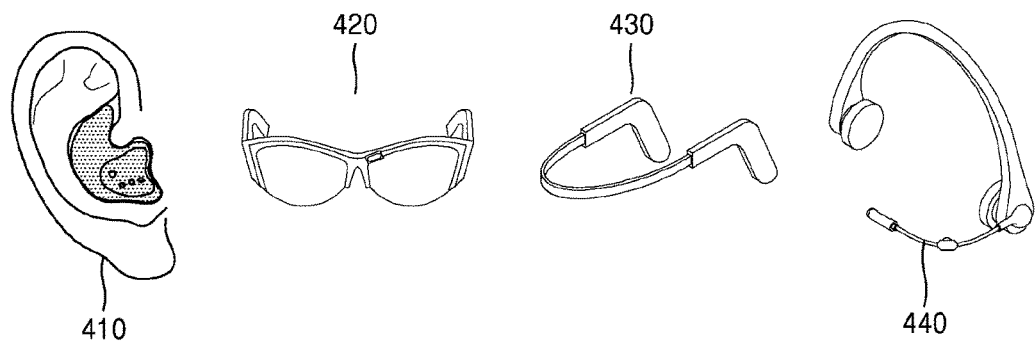
FIG. 8 illustrates examples of devices for measuring bio-signals, according to an exemplary embodiment.

FIG. 8 illustrates examples of devices for measuring bio-signals, according to an exemplary embodiment. The devices shown in FIG. 8 are examples of devices for measuring a brainwave signal, i.e., an EEG signal.

Referring to FIG. 8, according to an exemplary embodiment, the devices for measuring bio-signals (i.e., a brainwave signal) may be realized by an earphone 410, eyeglasses 420, a hair band 430, and a headset 440. Each of the devices supports a sound system to allow a user to listen to sounds of content therethrough.

However, the devices shown in FIG. 8 are only examples, and the devices may come in different forms.

A method of controlling a device based on bio-signals of a user will now be described in detail with reference to FIGS. 9 through 12. The device may be a wearable device such as smart glasses. Since a wearable device has a limited size, providing user inputs to the wearable device is difficult. According to an exemplary embodiment, a user may easily control a wearable device by using bio-signals that may be changed according to his or her will.

Figure 9:
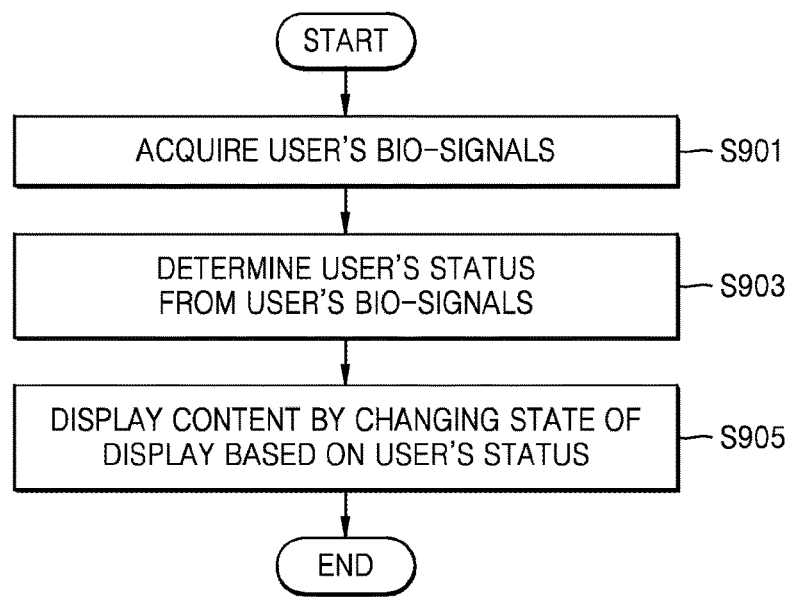
FIG. 9 is a flowchart of a method of displaying content by changing a state of a display based on a user's bio-signals, according to an exemplary embodiment.

FIG. 9 is a flowchart of a method of displaying content by changing a state of a display based on bio-signals of a user, according to an exemplary embodiment.

Referring to FIGS. 1 and 9, the device 100 may acquire bio-signals of a user (S901). The bio-signals may be signals used to detect a user's status, such as brainwaves and pulses. For example, brainwaves may be obtained by extracting EEG signals.

If the device 100 is a wearable device, the device 100 may be mounted on a user's body, and thus may include components for measuring the bio-signals. If the device 100 is smart glasses, the device 100 may be worn on the head to measure a brainwave signal.

A device for measuring a brainwave signal may be integrated with the device 100, but is not limited thereto. Such a device may be a head mounted sensor or in-ear sensor worn in an ear channel that is connected to the device 100 by wire or wirelessly. Alternatively, if the device 100 is realized by eyeglasses, the device 100 may include a sensor for measuring a brainwave signal that can be detachable from an upper rim of a glass frame of the eyeglasses.

A user's EEG signal obtained from the device for measuring a brainwave signal may be converted into values of amplitude in the time domain, power in the frequency domain, or power for each time. The device 100 may measure a user's brainwave signals at short time intervals of 1 to 5 seconds according to a value set by the user or a default value.

The device 100 may also perform bandpass filtering for removing specific frequencies to remove noise in the measured user's bio-signals. Furthermore, if the bio-signals are measured through a plurality of channels, the device 100 may perform filtering for spatially removing noise by using the bio-signals measured through the plurality of channels.

The device 100 may determine a user's current status from the bio-signals of the user that are measured in operation S901 (S903). The user's current status may include information about what the user desires to concentrate on or about whether the user desires to use a display.

In detail, the device 100 may determine whether the user desires to view a transparent display of smart glasses or a real view based on the bio-signals of the user. For example, the device 100 may determine the user's current status from EEG signals based on whether a user's concentration level remains greater than or equal to a reference value for a predetermined time. As another example, the device 100 may analyze a user's brainwave signals to determine that the user desires to view a display if a level of a workload generated by a user's stress and a user's will to view the display is greater than or equal to a reference value.

As another example, if a display is powered off or stays in a power save mode, the device 100 may determine a user's current status based on whether an event-related potential (ERP) occurs. ERPs are brainwaves recorded on the scalp and represent the brain's electrical response to a stimulus. ERP signals may be detected when the user is exposed to visual, auditory, olfactory, and tactile stimuli. If the detected ERP signals have a magnitude that is greater than or equal to a reference value, the device 100 may determine that the user is interested in a real object placed in a direction that the user views the real object and requires additional information about the real object, and turn on the display.

As another example, the device 100 may determine a user's current status from the user's EEG signals based on whether a user's focus changes to a near focus or a far focus. If the user's focus changes from a far focus to a near focus, the device 100 determines that the user desires to view a display in the form of eyeglasses and turn on the display. On the other hand, if the user's focus changes from a near focus to a far focus, the device 100 may determine that the user desires to see a real view and turn off the display.

As another example, the device 100 may display a dot blinking at unspecified frequencies on a transparent display in the form of eyeglasses and determine a user's current status by using the dot. In detail, if the user gazes at the blinking dot, the device 100 may detect an evoked potential (EP) corresponding to the blinking dot from brainwave signals. Furthermore, the device 100 may determine whether a user makes an effort to view content on the transparent display, based on a user's visual workload or stress level. The user's visual workload or stress level may be obtained from EEG signals or other types of brainwave signals. The device 100 may detect a user's intention to view the display by detecting the EP corresponding to the blinking dot and turn on the transparent display.

Referring back to FIG. 9, the device 100 may display content by changing a state of a display based on the user's current status determined in operation S903 (S905). In detail, the device 100 may turn on or off the display or control the display to stay in a power save mode, based on the user's current status.

Furthermore, the device 100 may control the state of the display by further using information about a result of analysis of an object located in a user's gaze direction, light intensity, and a light source. In detail, the device may 100 may determine a region on which content is displayed and a type of the content so as not to cover the object located in the user's gaze direction. For example, the device 100 may determine whether a text or image will be displayed according to the object located in the user's gaze direction. If the object has a high saturation, the device 100 may control a text to be displayed. As another example, the device 100 may determine a display reproduction parameter for optimally indicating a display based on information about a light intensity or light source and indicate the display according to the display reproduction parameter. The display reproduction parameter may include colors, brightness, contrast, transparency, focus, power supply, and power consumption of the display, and may correspond to the reproduction parameter described above with reference to FIGS. 1 through 3.

The display reproduction parameter may further include type of content being displayed. In other words, the display reproduction parameter may include a reproduction parameter for determining the type of content. For example, the device 100 may control another type of content to be output according to a level of a user's concentration on a display, which is determined from bio-signals of the user. If the user concentrates on the display, the device 100 may output visual content via the display. If the user does not concentrate on the display, the device 100 may output content by using a device for outputting an audio and speech signal or vibration signal instead of the display. Content that may be output via the device other than the display may include different types of content than visual content, such as audio or vibration content.

Figure 10:
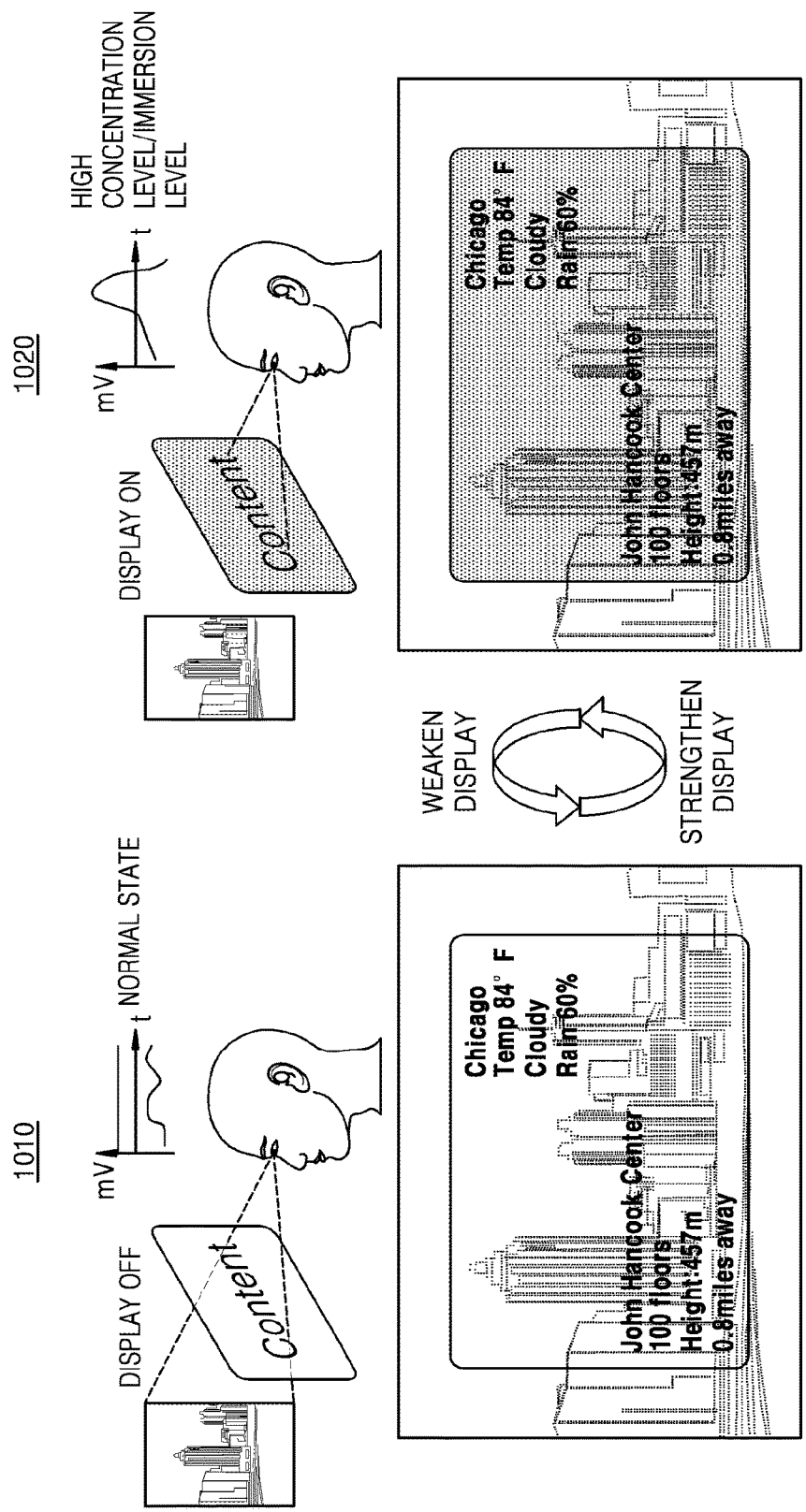
FIG. 10 illustrates an example where content is displayed by changing a state of a display based on a user's bio-signals, according to an exemplary embodiment.

FIG. 10 illustrates an example where content is displayed by changing a state of a display based on bio-signals of a user, according to an exemplary embodiment.

Referring to FIGS. 1 and 10, if the device 100 determines that a user is in a normal state, i.e., sees a real view, from brainwave signals of the user, the device 100 may turn off a display (1010). Alternatively, the device 100 may increase the transparency of the display so that the real view may be seen well via the display. The device 100 may allow the user to see the real view more clearly by controlling the display.

If the device 100 determines that the user has high concentration and immersion levels from the brainwave signals of the user, the device 100 may also determine that the user desires to view the display (1020). The device 100 may turn on the display and control the display so that the user may view the display more clearly than the real view.

Figure 11:
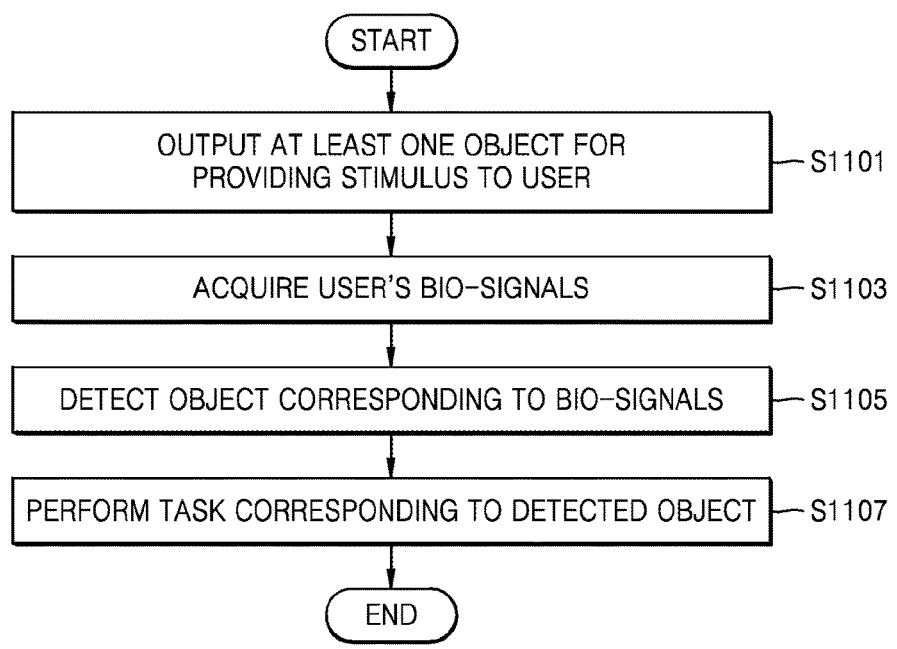
FIG. 11 is a flowchart of a method of performing a task based on a user's bio-signals, according to an exemplar embodiment.

FIG. 11 is a flowchart of a method of performing a task based on bio-signals of a user, according to an exemplary embodiment. In detail, the device 100 for performing the method of FIG. 11 may select a task that the user desires to perform based on a brainwave signal among the bio-signals of the user and perform the selected task. The device 100 may detect an ERP signal that is generated in response to a stimulus and select a task that the user desires to perform according to a magnitude of the ERP signal.

In detail, referring to FIG. 11, the device 100 may output at least one object for applying a stimulus to a user (S1101). For example, the device 100 may display an object for applying a stimulus to the user or output the object as an audio and speech signal or a vibration signal.

The device 100 may display at least one dot blinking at unspecified frequencies in order to give a visual stimulus to the user. At least one dot may be displayed according to the number of tasks that can be selected by the user. Since the user focuses on and gazes at a dot that the user desires to select, the device 100 may detect an ERP having a larger magnitude for the desired dot than for other dots. Dots may blink in a random order, and the device 100 may select a user's desired task by selecting a dot corresponding to a time point when an ERP signal has the largest magnitude.

As another example, the device 100 may output at least one object as an audio and speech signal or vibration signal in order to apply an auditory or tactile stimulus to the user. Each object may be output as an audio and speech signal or vibration signal that can be recognized by the user. When an object corresponding to a user's desired task is output, a concentration level or excitation level derived from a brainwave signal may be increased. Thus, an ERP signal having a larger magnitude may be detected when an object corresponding to a user's desired task is output than when another object is output. The device 100 may select a user's desired task by selecting an object corresponding to a time point when the ERP signal has a relatively large magnitude compared to another magnitude.

The object is not limited to signals for providing auditory, tactile, and visual stimuli, and may be output in various ways for applying other types of stimuli. The device 100 may select a user's desired task by selecting an object output when an ERP signal has a relatively large magnitude.

The device 100 may acquire bio-signals of the user (S1103). The bio-signals may be signals used to detect a user's status, such as brainwaves and pulses. For example, brainwaves may be obtained by extracting EEG signals.

The device 100 may detect an object corresponding to a response detected from the acquired bio-signals, i.e., brainwave signals (S1105).

When the user gazes at a dot displayed on a display, an ERP having a large magnitude may be detected during a time interval when the dot is displayed distinctly from other dots. For example, dots may flicker at unspecified or specific frequencies in a random order, or colors thereof may be changed so that only one dot is displayed distinctly from other dots during one time interval. The device 100 may detect an object corresponding to a response detected from brainwave signals by selecting a dot displayed at a time point when an ERP signal having a larger magnitude than that of another ERP signal is detected.

In addition to displaying an object for applying a visual stimulus, as described above, the device 100 may output an object for applying stimuli to the user in various ways. The device 100 may select a user's desired task by selecting an object output when an ERP signal has a relatively large magnitude.

The device 100 may perform a task corresponding to the object detected in operation S1105 (S1107). Each dot displayed on the display may correspond to a task that can be currently performed. The device 100 may perform a user's desired task corresponding to a dot determined based on the magnitude of an ERP signal, simply by detecting bio-signals that vary according to a user's desire without needing to receive a user's input via a button or touch.

Figure 12:
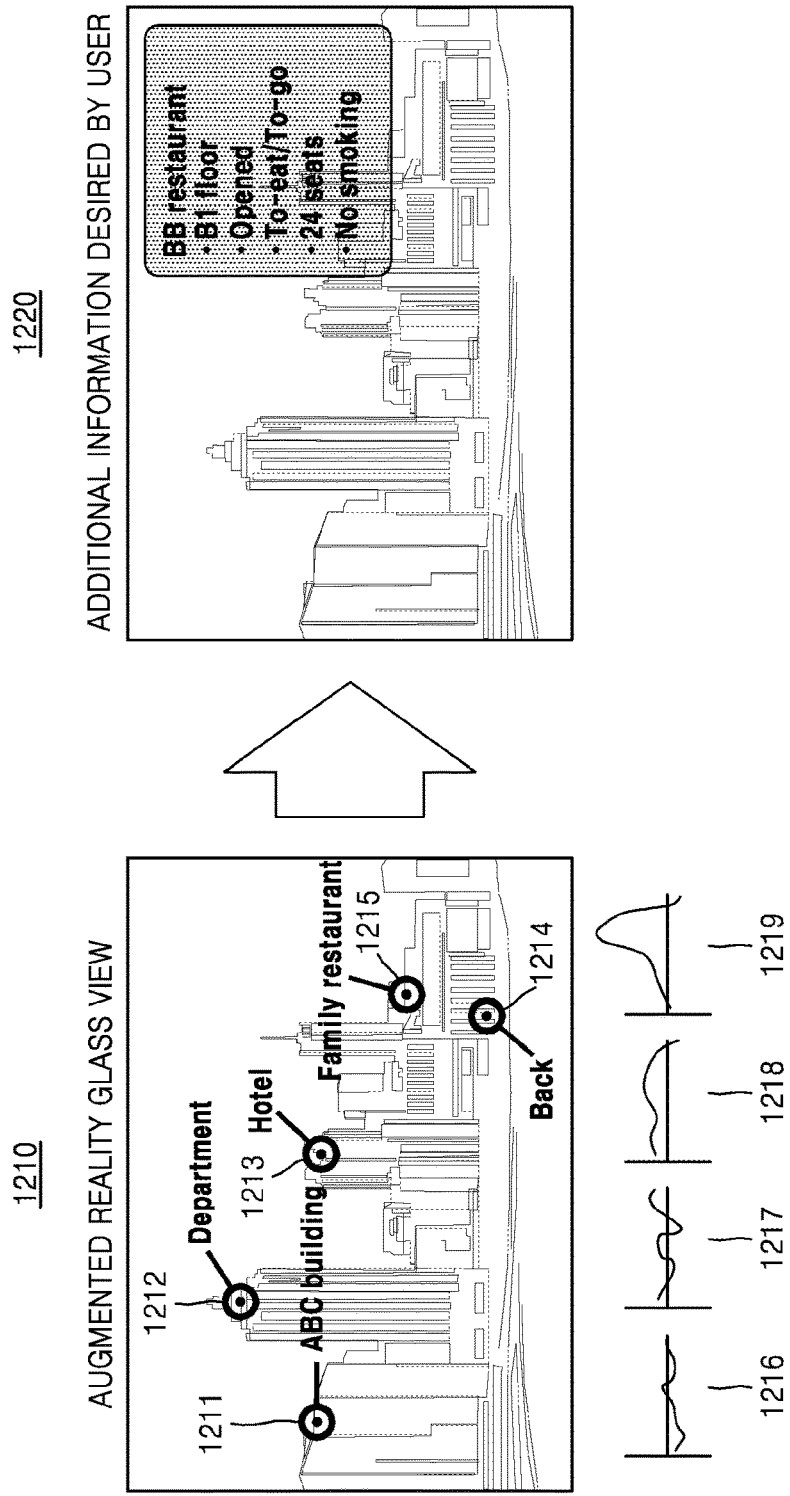
FIG. 12 illustrates an example where a task is performed based on a user's bio-signals, according to an exemplary embodiment.

FIG. 12 illustrates an example where a task is performed based on bio-signals of a user, according to an exemplary embodiment.

Referring to FIGS. 12, 1210 and 1220 illustrate examples of display screens of the device 100. If a display is equipped in a wearable device in the form of eyeglasses, the display may display an augmented reality screen by further indicating additional information of objects displayed on the display in addition to a screen captured via a camera of the wearable device. 1210 and 1220 illustrate examples of screens that further indicate additional information of objects displayed on the respective screens, compared to the augmented reality screens. In detail, 1210 shows an exemplary screen including buildings that may be selected by a user and dots 1211 through 1215 corresponding to the respective buildings, and 1220 shows an exemplary screen indicating additional information of a building selected by the user.

Referring to 1210, the dots 1211 through 1215 corresponding to objects appearing on the augmented reality screen may be displayed. By arranging the respective dots 1211 through 1215 so that they are separated from one another by maximum distances, a difference in magnitudes of ERP signals according to a user's concentration level may increase. As described above with reference to FIG. 11, the respective dots 1211 through 1215 may flicker at unspecified or specific frequencies in a random order, or colors thereof may be changed so that only one dot is displayed distinctly from other dots during one time interval. For example, each of the dots 1211 through 1215 may blink at frequency of about 4 Hz, or a color thereof may change at frequency of about 4 Hz. The period may be randomly changed.

User's brainwave signals 1216 through 1219 respectively correspond to the dots 1211 through 1215. If the user concentrates on and gazes at only one dot 1215, an ERP signal having a relatively large magnitude may be detected from the user's brainwave signal 1219 while the dot 1215 is being displayed in a specific color, as shown in FIG. 12, so that it is distinct from the other dots 1211 through 1214. The device 100 may select the dot 1215 corresponding to the ERP signal having a large magnitude and display additional information of an object corresponding to the selected dot 1215, as shown in 1220.

A method of performing authentication based on bio-signals of a user will now be described in detail with reference to FIGS. 13 through 15.

Figure 13:
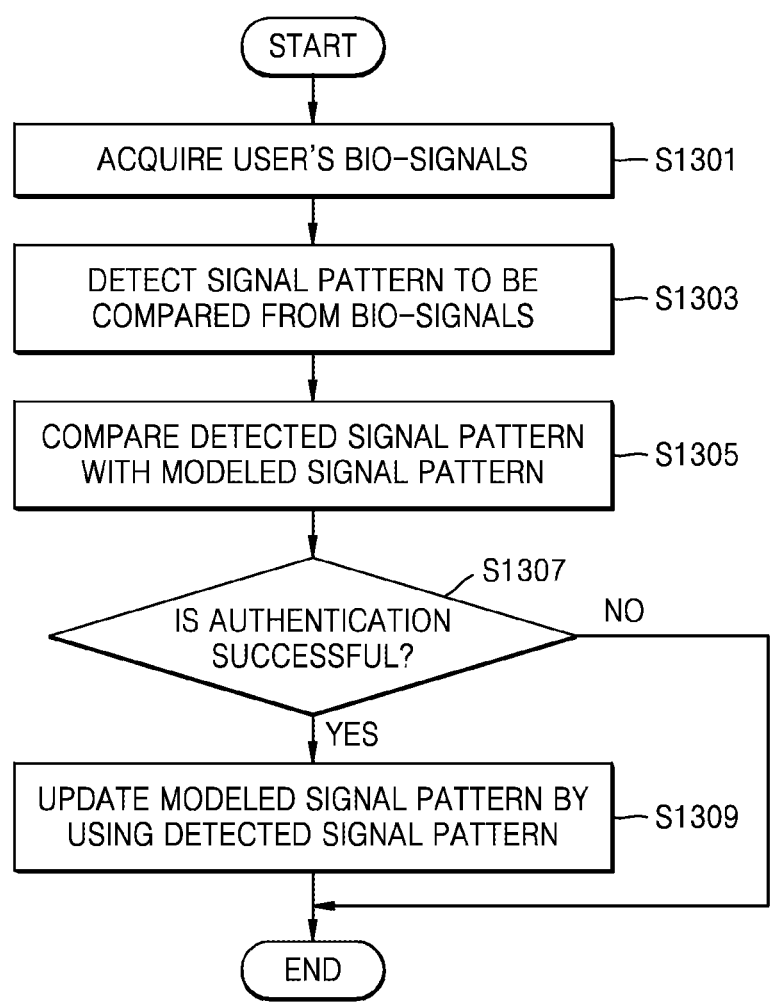
FIG. 13 is a flowchart of a method of performing authentication based on a user's bio-signals, according to an exemplary embodiment.

FIG. 13 is a flowchart of a method of performing authentication based on the bio-signals of the user according to an exemplary embodiment.

Referring to FIGS. 1 and 13, the device 100 may acquire bio-signals of a user (S1301). The bio-signals may be signals used to detect a user's status, such as brainwaves and pulses. For example, brainwaves may be obtained by extracting EEG signals.

The device 100 may detect a signal pattern to be compared against a modeled signal pattern from the bio-signals acquired in operation S1301 (S1303). If the bio-signals are brainwave signals, brainwave signals may have a signal pattern unique to an individual over a predetermined range. Thus, the device 100 may detect a signal pattern to be compared over a range in which a user's brainwave signal has a signal pattern unique to an individual and perform user authentication by comparing the detected signal pattern against a prestored modeled brainwave signal pattern.

The device 100 may perform user authentication by comparing the signal pattern to be compared, which is detected in operation S1303, against a modeled signal pattern (S1305). For example, since brainwave signals may vary depending on a user's status, a signal pattern to be compared and a modeled signal pattern may be slightly differently detected even for the same user. Thus, the device 100 may perform user authentication based on whether the signal pattern to be compared falls within a preset tolerance range of the modeled signal pattern.

If the user authentication is successful (S1307), the device 100 may update the modeled signal pattern by using the detected signal pattern (S1309). Furthermore, since the user authentication is successful, the device 100 may continuously perform a task that requires the user authentication.

On the other hand, if the user authentication failed in operation S1307, the device 100 may stop a task requiring the user authentication or may perform authentication by using another authentication method.

Since brainwave signals may vary according to a user's status or the surrounding environment, a modeled brainwave signal for user authentication requires a periodic update. Thus, even when a task requiring the user authentication is not performed, the device 100 may continuously measure brainwave signals to update modeled brainwave signals for the user authentication. The device 100 may also update modeled brain wave signals by using the measured brainwave signals, according to whether the measured brainwave signals fall within a tolerance range of the modeled brain wave signals. Alternatively, if the user authentication is already completed using other methods than use of brainwave signals, the device 100 may update modeled brainwave signals by using the measured brainwave signals without determining whether the measured brainwave signals fall within the tolerance range of the modeled brain wave signals.

The device 100 may update modeled brainwave signals for authentication by taking into account various factors that may change brainwaves such as information about the user's surrounding environment and user's status during measurement of brainwave signals. In detail, the device 100 may store the various factors such as information about the user's surrounding environment and user's status during measurement of brainwave signals together in modeled brainwave signals. Thus, the device 100 may perform user authentication by taking into account the various factors as well as the brainwave signals.

While a task requiring user authentication is being performed, the device 100 may repeatedly perform user authentication according to an exemplary embodiment. For example, if the user desires to make a transfer to a bank account via a bank application while wearing smart glasses, goggles, or wearable audio devices equipped with a sensor for measuring brainwave signals, the device 100 may repeatedly measure the user's brainwave signals and perform user authentication. That is, by repeatedly performing user authentication while the bank application is running, the device 100 may continue to check whether a user who initially has access to the bank application is the same as a user currently accessing the bank application.

Figure 14:
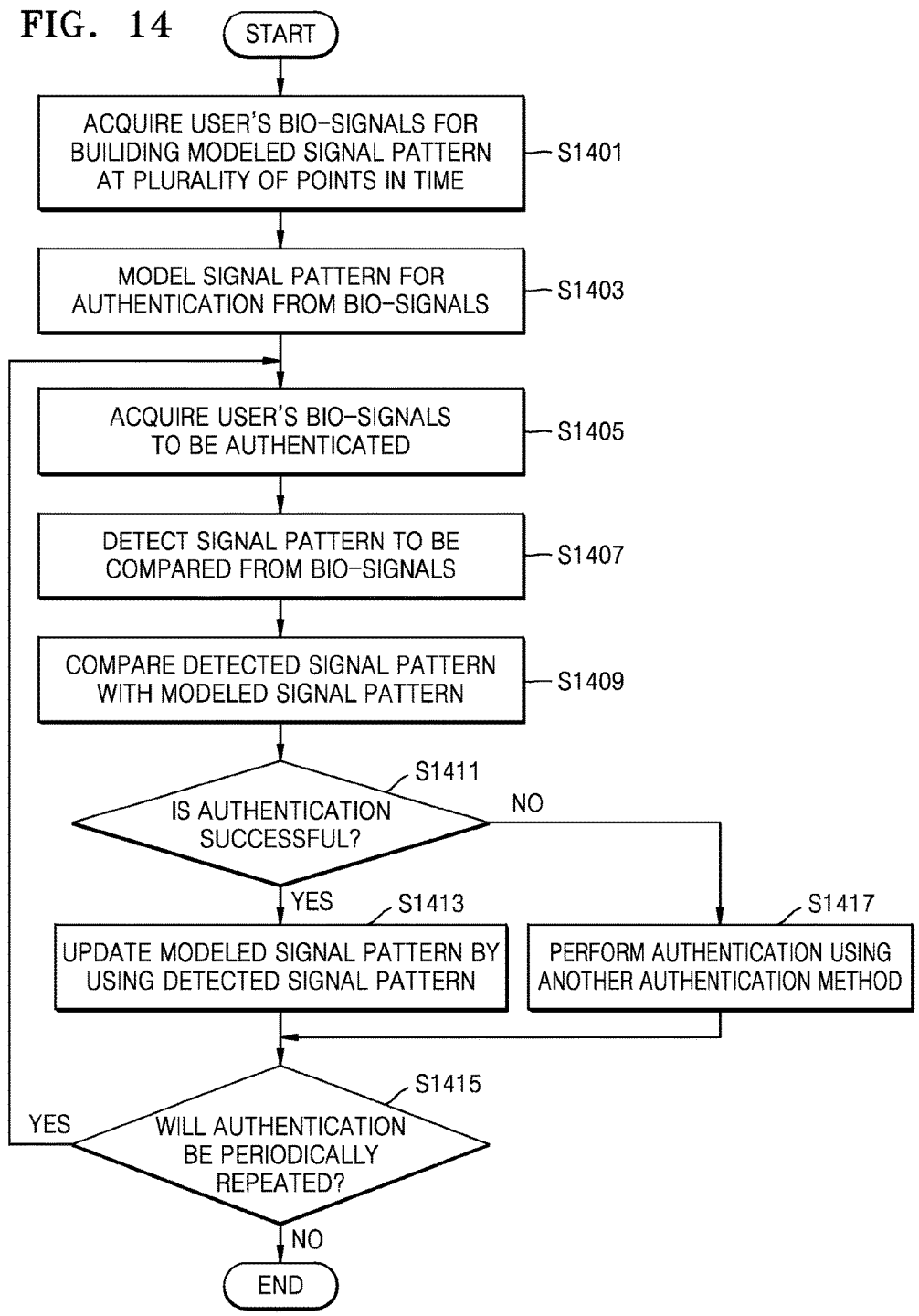
FIG. 14 is a flowchart of a method of performing user authentication based on a user's bio-signals, according to an exemplary embodiment.

FIG. 14 is a flowchart of a method of performing user authentication based on bio-signals of a user, according to an exemplary embodiment. Operations S1405 through S1413 correspond to operations S1301 through S1309, respectively.

Referring to FIGS. 1 and 14, the device 100 may acquire bio-signals of a user to build a modeled signal pattern at a plurality of points in time (S1401). Even when user authentication is not required, the device 100 may continuously measure brainwave signals in order to build the modeled signal pattern for user authentication.

The device 100 may model a signal pattern for user authentication based on the bio-signals of the user (S1403). For example, the device 100 may model a brainwave signal pattern for user authentication by detecting a portion of a user's brainwave signal having a signal pattern unique to each user.

When user authentication is required, the device 100 may acquire bio-signals of a user to be authenticated (S1405). The bio-signals acquired in operation S1405 may be signals used to detect a user's status, such as brainwaves and pulses. For example, brainwaves may be obtained by extracting EEG signals.

The device 100 may detect a signal pattern to be compared against a modeled signal pattern from the bio-signals acquired in operation S1405 (S1407). For example, the device 100 may detect a signal pattern to be compared from a user's brainwave signals and perform user authentication by comparing the detected signal pattern against a modeled brainwave signal pattern prestored in a database.

The device 100 may perform user authentication by comparing the signal pattern to be compared, which is detected in operation S1407, against a modeled signal pattern (S1409). In this case, the device 100 may perform user authentication based on whether the signal pattern to be compared falls within a preset tolerance range of the modeled signal pattern.

If the user authentication is successful (S1411), the device 100 may update the modeled signal pattern by using the detected signal pattern (S1413). Furthermore, since the user authentication is successful, the device 100 may continuously perform a task that requires the user authentication.

On the other hand, if the user authentication failed in operation S1411, the device 100 may stop a task requiring the user authentication or may perform authentication by using another authentication method (S1417). For example, if user authentication using brainwave signals failed, the device 100 may perform the user authentication by using various methods such as fingerprint recognition, iris recognition, input of a password, input of a correct pattern, etc.

The device 100 may determine whether a user authentication process will be periodically repeated, according to whether a task requiring user authentication is being performed (S1415). For example, when programs for a card payment or account transfer requiring user authentication are running, the device 100 may repeatedly perform operations S1405, S1407, S1409, S1411, S1413, S1415, and S1417. Since the device 100 according to the present embodiment may continuously perform user authentication without a user's physical input, user convenience and security may be enhanced.

The device 100 may perform authentication by comparing brainwave signals measured while the user maintains a resting state without thinking about or doing something against modeled brainwave signals. The modeled brainwave signals may be premodeled from brainwave signals measured while the user is in a resting state.

Figure 15:
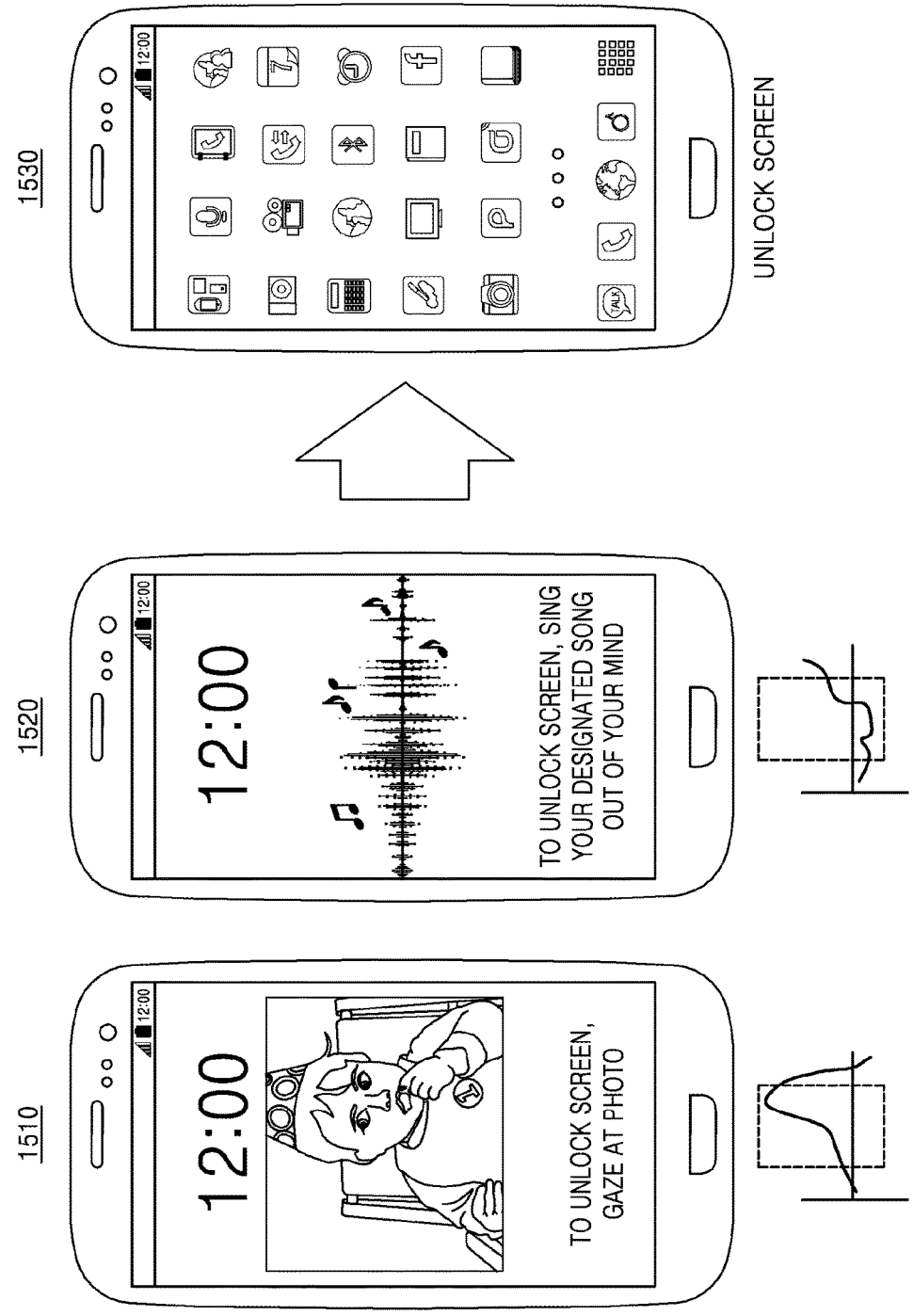
FIG. 15 illustrates an example where authentication is performed based on a user's bio-signals, according to an exemplary embodiment.

FIG. 15 illustrates an example where authentication is performed based on bio-signals of a user, according to an exemplary embodiment.

Referring to FIGS. 15, 1510, 1520, and 1530 illustrate examples of unlocking screens of smartphones by performing user authentication.

According to an exemplary embodiment, the device 100 may acquire bio-signals of a user corresponding to a state in which a specific stimulus is applied to the user and perform user authentication by comparing a signal pattern detected from the bio-signals with a modeled signal pattern that has been previously built. The modeled signal pattern may be built by modeling a part of a user's bio-signal corresponding to a state in which a specific stimulus is applied to the user and exhibiting unique characteristics In 1510 and 1520, the device 100 may measure bio-signals to be compared against a modeled signal pattern by applying a specific stimulus to the user. In detail, in 1510, the device 100 may instruct the user to gaze at a photo displayed in order to unlock a screen and measure a user's brainwave signal while the photo is being displayed. The modeled signal pattern to be compared with the user's brainwave signal may be built by detecting unique characteristics from a user's brainwave signal that is previously measured while the same photo was being displayed.

Furthermore, in 1520, the device 100 may instruct a user to have a predesignated music on his or her mind and measure a use's brainwave signal while such an instruction is being displayed. The modeled signal pattern to be compared with the user's brainwave signal may be built by detecting unique characteristics from a user's brainwave signal that is previously measured while an instruction for requesting the user to have the same music on his or her mind was being displayed.

The device 100 may compare the measured user's brain wave signal 1511 or 1521 with its corresponding modeled signal pattern and unlock the screen in 1530 if user authentication is successful.

Internal components of a device will now be described in detail with reference to FIG. 16.

Figure 16:
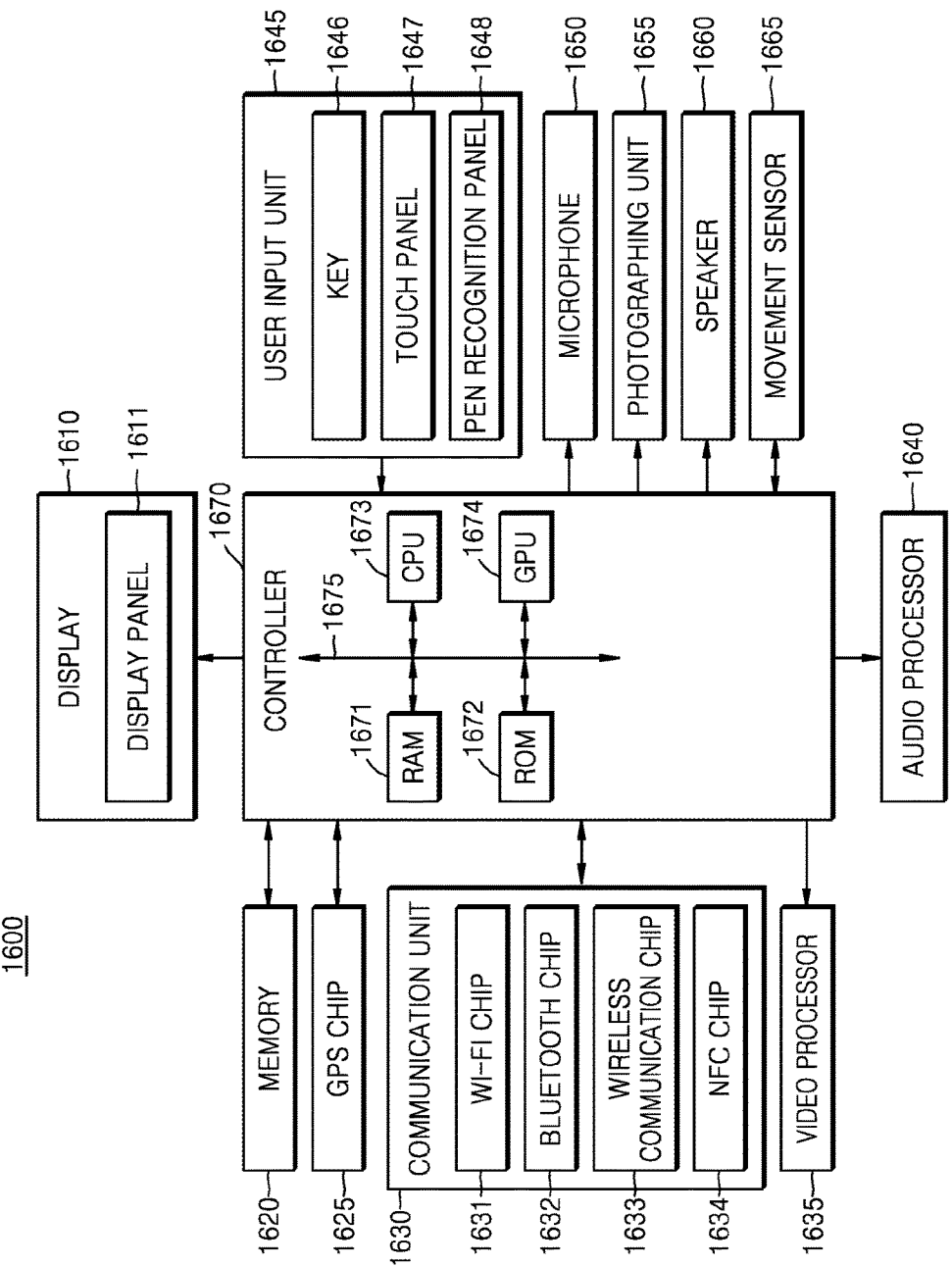
FIG. 16 is a block diagram of an internal configuration of a device for processing content or performing user authentication based on a user's bio-signals, according to an exemplary embodiment.

FIG. 16 is a block diagram of an internal configuration of a device 1600 for processing content or performing user authentication based on a user's bio-signals according to an exemplary embodiment. The device 1600 may correspond to the device 100 of FIG. 1.

Referring to FIG. 16, the device 1600 according to the present embodiment includes a display 1610, a memory 1620, a communication unit 1630, a controller 1670, a speaker 1660, a global positioning system (GPS) chip 1625, a video processor 1635, an audio processor 1640, a user input unit 1645, a microphone 1650, a photographing unit 1655, and a movement sensor 1665.

The display 1610 may include a display panel 1611 and a controller (not shown) for controlling the display panel 1611. Examples of the display panel 1611 include a Liquid Crystal Display (LCD), an Organic Light-Emitting Diode (OLED) display, an Active-Matrix OELD (AM-OLED) display, a Plasma Display Panel (PDP) display, and other displays. The display panel 1611 may be formed as a flexible, transparent, or wearable display. The display 1610 may be combined with a touch panel 1647 of the user input unit 1645 to form a touch screen. For example, the touch screen may include an integrated module in which the display panel 1611 is combined with the touch panel 1647 to form a layered structure.

According to an exemplary embodiment, the display 1610 may display an image corresponding to an audio signal output via the speaker 1660 according to control of the controller 1670. Images that may be displayed by the display 1610 may include two-dimensional (2D) or three-dimensional (3D) images.

The memory 1620 may include at least one of an internal memory (not shown) and an external memory (not shown).

The internal memory may include at least one of a volatile memory (e.g., Dynamic Random-Access Memory (DRAM), Static Random Access Memory (SRAM), Synchronous DRAM (SDRAM), and the like), a nonvolatile memory (e. g., One-Time Programmable Read-Only Memory (OT-PROM), Programmable ROM (PROM), Erasable PROM (EPROM), Electrically Erasable Programmable ROM (EE-PROM), mask ROM, flash ROM, and the like), a hard disk drive (HDD), and a solid-state drive (SSD). According to an exemplary embodiment, the controller 1670 may load a command or data received from a non-volatile memory or at least one of other components into a volatile memory for processing. Furthermore, the controller 1670 may store data received from or generated by other components in the non-volatile memory.

The external memory may include at least one of Compact Flash (CF), Secure Digital (SD), Micro-SD, Mini-SD, extreme Digital (xD), and a Memory Stick.

The memory 1620 may store various programs and data used for operation of the device 1600. According to an exemplary embodiment, at least one of an image, an audio signal corresponding to the image, and 3D image information may be stored temporarily or semi-permanently in the memory 1620.

The controller 1670 may control the display 1610 to display part of information stored in the memory 1620. For example, the controller 1670 may control the display 1610 to display images stored in the memory 1670. Alternatively, when a user performs a gesture on a region of the display 1610, the controller 1670 may perform a control operation corresponding to the gesture.

Although not shown in FIG. 2, the controller 1670 may include at least one selected from RAM 1671, ROM 1672, a central processing unit (CPU) 1673, a graphics processing unit (GPU) 1674, and a bus 1675. The RAM 1671, the ROM 1672, the CPU 1673, and the GPU 1674 may be connected to one another via the bus 1675.

The CPU 1673 accesses the memory 1620 and performs booting by using an operating system (O/S) stored in the memory 1620. The CPU 1673 also performs various operations by using various types of programs, content, and data stored in the memory 1620.

The ROM 1672 stores a set of commands to boot a system. For example, when a turn on command is input and power is supplied to the device 1600, the CPU 1673 may copy an O/S stored in the memory 1620 to the RAM 1671 according to a command stored in the ROM 1672, execute the O/S, and boot the system. When booting is completed, the CPU 1673 copies various programs stored in the memory 1620 to the RAM 1671, executes the programs copied to the RAM 1671, and performs various operations.

When booting of the device 1600 is completed, the GPU 1674 displays a UI screen on a region of the display 1610. In detail, the GPU 1674 may generate a UI screen including various objects such as content, icons, and menus. The UI screen according to an exemplary embodiment may be a UI screen used to output an image and an audio signal. The GPU 1674 calculates attribute values such as coordinate values, a shape, a size, and a color of each object to be displayed according to layouts of the screen. The GPU 1674 may also create a screen in various layouts, which include objects based on the calculated attribute values. The screen created by the GPU 1674 may be provided to the display 1610 so that it is displayed on each region of the display 1610.

The GPS chip 1625 may receive a GPS signal from a GPU satellite and calculate a current position of the device 1600. When the controller 1670 uses a navigation program or otherwise requires a user's current position, the controller 1670 may calculate the user's current position by using the GPS chip 1625. According to an exemplary embodiment, the GPS chip 1625 may identify an object located in a user's gaze direction based on a user's current position. Thus, the controller 1670 may determine a display reproduction parameter by analyzing the object located in the user's gaze direction and control the display 1610 to display contents according to the display reproduction parameter.

The communication unit 1630 may communicate with different types of external devices according to various types of communication methods. The communication unit 1630 may include at least one selected from the group consisting of a Wireless Fidelity (Wi-Fi) chip 1631, a Bluetooth chip 1632, a wireless communication chip 1633, and a Near Field Communication (NFC) chip 1634. The controller 1670 may communicate with various external devices via the communication unit 1630. For example, the controller 1670 may receive an image and an audio signal to be displayed on the display 1610 via the communication unit 1630.

The Wi-Fi chip 1631 and the Bluetooth chip 1632 may perform communication by using Wi-Fi and Bluetooth technologies, respectively. The communication unit 1630 using the Wi-Fi chip 1631 or the Bluetooth chip 243 may transmit or receive various kinds of information after transmitting or receiving various types of connection information such as service set identifiers (SSID) or session keys and establishing a communication connection by using the connection information. The wireless communication chip 1633 refers to a chip that performs communication according to various communication standards such as the Institute of Electrical and Electronics Engineers (IEEE), ZigBee, Third Generation (3G), Third Generation Partnership Project (3GPP), and Long Term Evolution (LTE). The NFC chip 1634 refers to a chip that performs communication by using NFC technology that operates at a 13.56 MHz frequency band among various radio frequency identification (RFID) frequency bands including 135 kHz, 13.56 MHz, 433 MHz, 860 to 960 MHz, and 2.45 GHz.

The video processor 1635 may process image data received via the communication unit 1630 or stored in the memory 1620. The video processor 1635 may perform various types of image processing, such as decoding, scaling, noise filtering, frame-rate conversion, and resolution conversion, on image data. The display 1610 may also display image data processed by the video processor 1635.

The audio processor 1640 may process audio data received via the communication unit 1630 or stored in the memory 1620. The audio processor 1640 may perform various types of processing, such as decoding, amplification, and noise filtering, on audio data. For example, the audio processor 1640 may process audio data corresponding to an image displayed on the display 1610. Furthermore, the audio processor 1640 and the video processor 1635 may process audio data and video data according to a reproduction parameter determined based on a user's bio-signals, respectively.

When a reproduction program for multimedia content is executed, the controller 1670 may drive the video processor 1635 and the audio processor 1640 to reproduce the multimedia content. The speaker 1660 may output audio data generated by the audio processor 1640. For example, the controller 1670 may control the video processor 1635 and the audio processor 1640 to process multimedia content displayed on the display 1610.

The user input unit 1645 may receive various commands from a user. The user input unit 1645 may include at least one of a keypad 1646, a touch panel 1647, and a pen recognition panel 1648. The device 1600 may output an image and an audio signal according to a user input received from at least one of the keypad 1646, the touch panel 1647, and the pen recognition panel 1648.

The keypad 1646 may include various types of keys such as mechanical buttons, wheels, etc., provided on various regions such as a front surface, a side surface, and a rear surface of a main body of the device 1600.

The touch panel 1647 may detect a user's touch input and output a touch event value corresponding to a detected touch input. When the touch panel 1647 is combined with the display panel 1611 to form a touch screen (not shown), the touch screen may be realized as various types of touch sensors such as capacitive, resistive, and piezoelectric touch sensors. A capacitive touch sensor uses a dielectric material coated on a surface of a touch screen. When a part of a user's finger touches a surface of the touch screen, the capacitive touch sensor detects small electrical charges caused by the part of the user's finger and calculates touch coordinates. A resistive touch sensor includes two upper and lower electrode plates embedded in a touch screen, and when a user touches a specific point on the screen, the upper and lower electrode plates are brought into contact at the touched point. In this case, the resistive touch sensor detects flow of current caused by the contact and calculates touch coordinates. A touch event on the touch screen may mostly be generated using a human's fingers. However, the touch event may also occur via an object formed of a conductive material that may cause a change in capacitance.

The pen recognition panel 1648 senses a pen's proximity input or touch input according to a manipulation of a touch pen (e.g., a stylus pen or a digitizer pen) and outputs a pen proximity event or pen touch event corresponding to the sensed pen's proximity input or touch input. The pen recognition panel 1648 may be realized using an Electro Magnetic Resonance (EMR) technique and sense a touch input or proximity input according to a variation in the strength of an electromagnetic field caused by the pen's proximity or touch. In detail, the pen recognition panel 1648 may include an electromagnetic induction coil sensor (not shown) having a grid structure and an electric signal processor (not shown) that sequentially provides alternating current (AC) signals having a predetermined frequency to loop coils of the electromagnetic induction coil sensor. When a pen having a resonant circuit therein is disposed close to a loop coil of the pen recognition panel 1648, a magnetic field transmitted from the loop coil generates current based on mutual electromagnetic induction in the resonant circuit of the pen. An induction field is created from a coil of the resonant circuit in the pen, based on the current. The pen recognition panel 1648 then detects the induction field from a loop coil that is in a signal reception state and senses the position of a point that the pen is held in close proximity to and touches. The pen recognition panel 1648 may be disposed below the display panel 1611 and have a sufficient area so as to cover a display area of the display panel 1611.

Furthermore, the user input unit 1645 according to an exemplary embodiment may receive a user input by measuring a user's bio-signals. For example, since a magnitude of an ERP signal among the user's brainwave signals may vary according to the user's will, the user input unit 1645 may receive a user input based on the magnitude of an ERP signal. In detail, the user input unit 1645 may perform a task by selecting an object output at a time point when an ERP signal has a relatively large magnitude.

The microphone 1650 receives a user's voice or other sounds and converts the user's voice or the other sounds into audio data. The controller 1670 may use the user's voice input via the microphone 1650 for calling operations, or may convert the user's voice into audio data for storage in the memory 1620.

The photographing unit 1655 may capture still or moving images according to a user's control. The photographing unit 1655 may be realized using a plurality of cameras such as a front camera and a rear camera. The controller 1670 according to an exemplary embodiment may acquire information about a user's external environment from an image captured by the photographing unit 1655. The controller 1670 may determine a parameter for facilitating an optimal display based on the information about the user's external environment.

When the device 1600 includes the photographing unit 1655 and the microphone 1650, the controller 1670 may perform control operations according to a user's voice input via the microphone 1650 or a user's motion recognized by the photographing unit 1655. For example, the device 1600 may operate in a motion control mode or voice control mode. When the device 1600 operates in a motion control mode, the controller 1670 may activate the photographing unit 1655 to photograph a user, track a change in a user's motion, and perform a control operation corresponding to the change. For example, the controller 1670 may output an image and an audio signal according to an input of a user's motion recognized by the photographing unit 1655. When the device 1600 operates in a voice control mode, the controller 1670 analyzes a user's voice input via the microphone 1650 and performs a control operation according to the analyzed user's voice.

The movement sensor 1665 may detect a movement of a main body of the device 1600. The device 1600 may rotate or be tilted in various directions. In this case, the movement sensor 1665 may detect motion characteristics such as a direction and an angle of rotation and a slope by using at least one of various sensors such as a geomagnetic sensor, a gyro sensor, and an accelerometer. For example, the movement sensor 1665 may receive a user input by detecting a movement of the main body of the device 1600 and output an image and an audio signal according to the received user input.

Although not shown in FIG. 16, according to an exemplary embodiment, the device 1600 may further include a Universal Serial Bus (USB) port to which a USB connector can be connected, various external input ports for providing a connection to various types of external terminals such as a headset, a mouse, and a local area network (LAN), a Digital Multimedia Broadcasting (DMB) chip for receiving and processing a DMB signal, and various types of sensors.

The names or appellations of the above components of the device 1600 may be changed. Furthermore, the device 1600 according to the present inventive concept may include at least one of the above components. Some of the components may be omitted, and the device 1600 may include other components than the ones described above.

According to an exemplary embodiment, characteristics of content being reproduced may be altered according to a user's status detected from his or her brainwave signals, thereby allowing the user to identify his or her status and change the status in a positive direction.

According to an exemplary embodiment, a user input is facilitated by not having to input via physical contact, and thus, the convenience of user manipulation may be improved.

According to an exemplary embodiment, by using a user's brainwave signals, user authentication is performed without having to input via physical contact. Thus, the user authentication may be performed in a highly secure and convenient way.

The methods according to the above exemplary embodiments can be implemented on a computer-readable recording medium as codes that can be read by a computer (including all devices having information processing capabilities). The computer-readable recording medium is any recording media having stored thereon data that can be read by a computer system. Examples of the computer-readable recording medium include ROM, RAM, CD-ROM, magnetic tapes, floppy disks, and optical data storage devices.

While the above descriptions that apply to various embodiments of the present inventive concept are focused on new features of the present inventive concept, it will be understood by those of ordinary skill in the art that various deletions, substitutions, and changes in form and details of the systems and methods described above may be made therein without departing from the spirit and scope of the present inventive concept as defined by the following claims. The scope of the inventive concept is defined not by the detailed description of the inventive concept but by the appended claims, and all differences within the scope of the appended claims and their equivalents will be construed as being included in the present inventive concept.

The invention claimed is:

1. A method of processing content based on at least one bio-signal, the method comprising:
   outputting a content including at least one from among audio content and image content;
   acquiring information related to the at least one bio-signal of a user with respect to the content;
   determining a parameter for processing of the content, based on the acquired information related to the at least one bio-signal;
   processing the content, based on the determined parameter;
   outputting the processed content;

determining a concentration level of the user based on the at least one bio-signal;

obtaining information related to the content while the determined concentration level of the user is less than a reference point; and providing to the user the obtained information related to the content if the concentration level of the user is greater than or equal to the reference point, or according to a user's input.

2. The method of claim 1, wherein the determining of the parameter comprises:

determining at least one selected from a group consisting of a user's emotional state, sleep state, stress, workload, and concentration level, based on the acquired information related to at least one bio-signal; and determining the parameter corresponding to the determined user's state.

3. The method of claim 1, wherein the at least one bio-signal comprises a brainwave signal of the user, and wherein the parameter is determined based on a user's state corresponding to at least one property of the brainwave signal in a time or frequency domain.

4. The method of claim 1, wherein the parameter comprises at least one selected from a group consisting of a volume, pitch, playback speed, richness of sound, depth, reverberation, thickness, vibration, sensory effect, surround effect, spatial sense, harmony, chord and accompaniment of the content, a region on a display where the content is displayed, and colors, brightness, contrast, transparency, focus, power supply, and power consumption of the display.

5. The method of claim 1, further comprising:

outputting at least one object for providing a stimulus to the user;

acquiring information related to the at least one bio-signal of the user, which is generated while or after outputting the at least one object;

detecting an object corresponding to a response detected from the at least one bio-signal of the user, from among the at least one object; and performing a task corresponding to the detected object.

6. The method of claim 1, wherein the information related to the content includes at least one of main details and summary information of the content at a time point when the concentration level of the user decreases to less than the reference point.

7. The method of claim 1, wherein the information related to the content is acquired based on at least one selected from a group consisting of big data, per-minute audience ratings, and basic information related to the content that are acquired from an external server.

8. A device for processing content based on at least one bio-signal, the device comprising:

an outputter configured to output a content including at least one audio content and image content;

a bio-sensor configured to acquire information related to the at least one bio-signal of a user with respect to the content; and at least one processor configured to determine a parameter for processing of the content based on the acquired information related to the at least one bio-signal and process the content based on the determined parameter;

wherein the outputter is further configured to output the processed content, wherein the at least one processor is further configured to determine a concentration level of the user based on the acquired information related to the at least one bio-signal and obtain information related to the content while the determined concentration level of the user is less than a reference point, and wherein the outputter is further configured to provide to the user the obtained information related to the content if the concentration level of the user is greater than or equal to the reference point, or according to a user's input.

9. The device of claim 8, wherein the bio-sensor acquires the information related to the at least one bio-signal of the user generated while or after outputting at least one object for providing a stimulus to the user, and wherein the at least one processor detects an object corresponding to a response detected from the at least one bio-signal of the user, from among the at least one object and performs a task corresponding to the detected object.

10. The device of claim 8, wherein the at least one bio-signal of the user is at least one from among electroencephalogram (EEG), electrooculogram (EOG), electrocardiogram (ECG), electromyogram (EMG), and electrokardiogramm (EKG) signal.

* * * * *